_United States Patent_ [19]

Grögler et al.

[11] Patent Number: 4,483,974

[45] Date of Patent: Nov. 20, 1984

[54] PROCESS FOR THE PRODUCTION OF STABILIZED POLYISOCYANATES, THE POLYISOCYANATES SO-STABILIZED AND THEIR USE IN THE PRODUCTION OF POLYURETHANES

[75] Inventors: Gerhard Grögler; Heinrich Hess, both of Leverkusen; Richard Kopp, Cologne, all of Fed. Rep. of Germany

[73] Assignee: Bayer Aktiengesellschaft, Leverkusen, Fed. Rep. of Germany

[21] Appl. No.: 514,410

[22] Filed: Jul. 18, 1983

[30] Foreign Application Priority Data

Aug. 18, 1982 [DE] Fed. Rep. of Germany ....... 3230757

[51] Int. Cl.$^3$ ..................... C08G 18/32; C08G 18/48; C08G 18/14
[52] U.S. Cl. ...................................... 528/68; 428/403; 528/44; 528/85; 521/51; 252/188.31
[58] Field of Search ....................... 528/44, 68, 45, 85; 252/188.31; 428/403; 521/51

[56] References Cited

U.S. PATENT DOCUMENTS

| | | | |
|---|---|---|---|
| 2,800,457 | 7/1957 | Green et al. ......................... | 252/316 |
| 2,858,298 | 10/1958 | Burt ..................................... | 260/77.5 |
| 3,325,421 | 6/1967 | Mueller ............................... | 252/308 |
| 3,409,461 | 11/1968 | Mehlo et al. ........................ | 117/100 |
| 3,475,200 | 10/1969 | Kallert et al. ....................... | 117/94 |
| 3,551,346 | 12/1970 | Breen et al. ......................... | 252/316 |
| 3,577,515 | 5/1971 | Vandegaer ........................... | 424/32 |
| 3,900,669 | 5/1975 | Kiritani .............................. | 428/307 |
| 3,933,759 | 1/1976 | Hoeschele .......................... | 528/68 |
| 3,963,680 | 6/1976 | O'Keefe et al. ..................... | 528/44 |
| 4,046,741 | 9/1977 | Scher .................................. | 528/68 |
| 4,070,346 | 1/1978 | Schnöring et al. .................. | 528/68 |
| 4,089,835 | 5/1978 | König et al. ........................ | 528/68 |
| 4,119,565 | 10/1978 | Baatz et al. ......................... | 521/76 |
| 4,400,497 | 8/1983 | Blum et al. .......................... | 528/45 |

FOREIGN PATENT DOCUMENTS 2557407 6/1977 Fed. Rep. of Germany .
3112054 10/1982 Fed. Rep. of Germany .
1134285 11/1968 United Kingdom .

_Primary Examiner_—Herbert S. Cockeram
_Attorney, Agent, or Firm_—Gene Harsh; Joseph C. Gil

[57] ABSTRACT

A process for the production of solid polyisocyanates stabilized by a polymer coating and showing retarded reactivity comprising reacting (1) one or more solid polyisocyanates in particulate form, said polyisocyanates having melting points above 30° C., and
(2) from 0.1 to 25 equivalent percent of amine per isocyanate equivalent of an organic compound having a molecular weight of from 32 to 6000, said organic compound being selected from the group consisting of
  (a) di- or higher functional compounds containing 2 or more aliphatically-bound primary and/or secondary amino groups,
  (b) compounds containing one or more terminal —CO—, —NH—, —NH$_2$— groups,
  (c) hydrazines, and
  (d) mixtures thereof said reaction being conducted at a temperature below the melting temperature of said solid polyisocyanate, and being conducted in the presence of (3) a liquid medium selected from the group consisting of
  (a) organic compounds containing one or more hydroxy groups and having molecular weights of from 62 to 6000,
  (b) organic compounds containing 2 or more aromatically-bound amino groups and having molecular weights of from 108 to 6000,
  (c) organic compounds containing 2 or more aliphatically-bound amino groups and having molecular weights of from 400 to 6000,
  (d) plasticizers,
  (e) water, and
  (f) mixtures thereof to form a suspension of polyadduct-coated, stabilized polyisocyanate in the liquid medium.

52 Claims, No Drawings

PROCESS FOR THE PRODUCTION OF STABILIZED POLYISOCYANATES, THE POLYISOCYANATES SO-STABILIZED AND THEIR USE IN THE PRODUCTION OF POLYURETHANES

BACKGROUND OF THE INVENTION

This invention relates to a process for the production of solid polyisocyanates stabilized by a polymer coating and having retarded reactivity. The stabilized polyisocyanates are prepared by reacting solid, finely particulate polyisocyanates with di- and/or higher functional compounds containing aliphatically bound amino groups and/or terminal —CO.NH—NH$_2$-groups and/or hydrazine(s) in a quantity of from 0.1 to 25 equivalent percent of "amine" per equivalent of NCO in a liquid medium of monoalcohols and/or polyols and/or polyamines and/or plasticizers and/or water (optionally in the presence of apolar or slightly polar solvents) to form a suspension of polyadduct-coated, stabilized polyisocyanates in the liquid medium. The resultant polyisocyanates may be isolated, optionally by filtration and then suspended in polyols and/or polyamines.

The invention also relates to polyadduct-coated polyisocyanates obtained by the above process in finely particulate form, preferably suspended in low molecular weight and/or relatively high molecular weight polyols and/or in low molecular weight and/or relatively high molecular weight aromatic and/or relatively high molecular weight aliphatic polyamines, characterized by a 0.1 to 25% conversion of the NCO-groups and by a higher "thickening temperature" than the corresponding unstabilized polyisocyanates.

The present invention also relates to the use of the stabilized polyadduct-coated polyisocyanates optionally suspended in polyols and/or polyamines as reaction components in polyurethane syntheses, preferably using aromatic polyamines as chain-extending agents. More particularly, the compositions of the present invention may be used in hardenable reactive polyurethane systems having a long pot life.

The one-component reactive mixture can be converted into polyurethanes, preferably by thermal hardening, optionally using lead and/or tin catalysts.

Storable one-component systems based on polyisocyanates which are solid at room temperature and which show high stability in storage, even with respect to aromatic polyamines, have never been described before. There are also very few publications on the surface modification of polyisocyanates solid at room temperature.

German Offenlegungsschrift No. 25 57 407 describes a process in which a solution of a polyisocyanate in a low-boiling solvent is sprayed into a reactor with gaseous di- and/or polyamine, the reaction occurring between the polyisocyanate and the amine. The reaction is followed by evaporation of the solvent, yielding hollow polyurethane polyurea beads which are preferably used as fillers. The reaction is carried out in such a way that virtually all the NCO-groups react with the amine and with any other NCO-reactive components added. There is no indication of the reaction being carried out in such a way that the polyurea coating makes up only a fraction of the solid. There is also no indication that unreacted NCO-groups in the interior are available for further reactions in the sense of a one-component polyurethane system.

U.S. Pat. No. 3,409,461 describes the coating of polyisocyanates with a protective substance, preferably a polymer, as a result of which the polyisocyanate particles are surface-deactivated. To accomplish this, the isocyanate is dispersed in a solution of the polymer in a low-boiling solvent which does not dissolve the isocyanate to any significant extent. The dispersion thus formed is spray-dried. In a preferred embodiment, finely ground (particle size of from 1 to 10 μm) naphthylene-1,5-diisocyanate is spray-dried with a 1 to 2.5% solution of polystyrene, polyvinyl butylether, chlorinated rubber and the like in tetrachloromethane. Free-flowing powders having a particle size of from about 1 to 50 μm are obtained. They are preferably used for improving the adhesion of polyester products (fabrics, fibers, films) to rubber elastomers. In this process, it is necessary to use considerable quantities of solvents (which may be toxic), for example 4 kg of tetrachloromethane for 50 g of naphthylene-1,5-diisocyanate, which then must be removed by an energy-consuming process. One particular disadvantage of the process is the considerable contribution of the coating to the total weight of the coated isocyanate, amounting to between 9 and 91% by weight and generally to around 50% by weight. An excessive percentage of troublesome foreign substance would, thus, be introduced in the production of high-quality polyurethanes.

U.S. Pat. No. 3,551,346 describes the encapsulation of liquid diisocyanates by interfacial reactions of CH$_3$—Si—(OCH$_3$)$_3$ dissolved in the diisocyanate with (CH$_3$)$_3$.Si—O—Na dissolved in the aqueous phase, the reactions being accompanied by film formation. These droplets pre-encapsulated by the formation of silicone polymers are then "encapsulated" by coacervation (for example with oppositely charged polymers in accordance with U.S. Pat. No. 2,800,457).

German Offenlegungsschrift No. 15 70 548 describes a one-component system of prolonged stability which consists of a mixture of 1 mole of a polyester, polyether or polythioether, at least 1.5 moles of a solid isocyanate containing uret dione groups and having a melting point of ≧100° C. and at least 0.3 mole of a solid chain-extending agent containing OH— and/or NH$_2$—groups and having a melting point of ≧80° C. In this known system, at least 80% of the solid constituents of the mixture have to have a particle size of ≦30 μm. The stability of the product in storage at room temperature amounts to between a few days and a few weeks and, at 50° C., to only a few hours. One of the disadvantages of the process lies in the fact that, of three reactants, at least two must be present in solid form to guarantee the requisite stability in storage. As a result, the viscosity of the mixture obtained is generally very high and continues to increase slowly because none of the compounds is modified in its reactivity.

The reaction on the surface of the solid particles, which is reflected in the continuous increase in viscosity, takes place without control and too slowly for practical purposes and does not retard the reactivity of the polyisocyanates sufficiently for the system to become self-stabilizing. In addition, the high percentages of solid constituents can be expected to give rise to inhomogeneities in the heated product during hardening of the mixture. In addition, difficulties are involved in processing the highly viscous or solid mixtures because, in contrast to liquid mixtures, they have first to be brought into a formable state by an increase in temperature or by the application of pressure. The residence of high-melting polyisocyanates in mixtures of high and low molecular weight polyols is accompanied by a continuous and relatively fast further reaction producing a considerable increase in viscosity. In other words, the surface reaction on the solid polyisocyanate particles does not form a coating around the polyisocyanate which is sufficient to retard its reactivity, i.e. which has an adequate stabilizing effect.

British Patent No. 1,134,285 describes a process for the production of dimeric diisocyanates in an aqueous reaction medium. According to this patent, the dimers thus produced in aqueous suspension do not react with polyfunctional compounds containing active hydrogen atoms at room temperature, but instead may be thermally crosslinked to form polyurethanes. Stability may possibly be brought about by a slow surface reaction of isocyanate groups with water. Crosslinking is subsequently obtained by splitting of the uret dione ring at elevated temperatures, for example at temperatures in the range from 150° to 200° C.

DESCRIPTION OF THE INVENTION

By contrast, the object of the present invention is to provide solid polyisocyanates of retarded reactivity formed by reaction with the amine stabilizers of the present invention, i.e., polyamines, hydrazine(s) or hydrazide compounds containing terminal —CO.NH.NH$_2$— groups. The polyisocyanates are stabilized by coating with polyaddition products ("polyadducts"), the coating being formed essentially from polyadducts in a thin layer and through only minimal reaction of the NCO— groups at the surface of the solid isocyanate particles. The stabilization reaction involving the polyadduct coating gives polyisocyanate particles which only react as polyisocyanates in one-component systems above a certain "thickening temperature" to be defined hereinafter, or through bursting open of the polyadduct coating, through destruction of the coating by shear forces or through facilitation of the diffusion of the polyisocyanates through the polyadduct layer or even through dissolution of the polyadduct layer by polar solvents.

The "polyadduct" coating around the solid polyisocyanate particles differs slightly depending on the type of amine stabilizer used. Where polyamines are used, polyurea coatings are formed; where hydrazine(s) is-/are used, polyhydrazodicarbonamide coatings are formed; where hydrazide compounds containing terminal CO—NH—NH$_2$-groups (such as dihydrazides, bis-semicarbazides, bis-carbazinic esters, semi-carbazide hydrazides or aminohydrazides) are used, the polyadducts formed are more complex, containing a plurality of differently arranged —NH— and —CO-groups in the polymer chain.

The stabilized polyisocyanates are preferably produced directly in suspension in polyols and/or polyamines, preferably in relatively high molecular weight polyols, optionally in the presence of low molecular weight polyols or aromatic polyamines as chain-extending agents. The stabilized polyisocyanates are also preferably prepared in relatively high molecular weight polyamines containing aromatic and/or aliphatic amino groups, optionally in the presence of low molecular weight aromatic polyamines and/or low molecular weight polyols as chain-extending agents. The resultant stabilized polyisocyanates are thus present in the form of a suspension which may be further used as one-component polyurethanes.

In addition to the above-noted in situ production, the stabilized polyisocyanates may also be produced by reaction in monoalcohols, plasticizers and/or water. The stabilized, coated polyisocyanates formed may be separated off (for example by filtration), isolated and then suspended in polyols and/or polyamines.

Regardless of how they are formed, the stabilized polyisocyanates of the present invention still contain from at least 75% to at most 99.9% of the isocyanate groups of the unmodified isocyanates. Preferably the stabilized polyisocyanates contain from 92% (and preferably from 97%) to 99.7% of the isocyanate groups of the unmodified isocyanate.

It has been found that, using the "amine stabilizers" [i.e. difunctional and/or higher, low molecular weight and/or relatively high molecular weight aliphatic polyamines, polyhydrazide compounds containing terminal CO—NH—NH$_2$-groups and/or hydrazine (s)], a polyadduct coating can be obtained with very small quantities expressed as equivalent percent. To obtain nonporous, "elastic" polyadduct coatings, it is preferred to work in the presence of a liquid medium, such as monoalcohols and/or polyols and/or polyamines and/or plasticizers and/or water. In the case of amine stabilizers having an elasticizing effect (as is the case for example with relatively high molecular weight polyether polyamines containing terminal aliphatic amino groups or higher molecular compounds containing terminal —CO—NH—NH$_2$-groups), the liquid medium need not be used since such amine stabilizers will act as both amine stabilizer and liquid medium.

The stabilized polyisocyanates show extremely high stability in storage in the suspended polyols and/or even in relatively high molecular weight polyamines, even at elevated temperatures and even in the presence of highly active polyurethane catalysts. When the coated polyisocyanates of the invention are used, reactive PU-mixtures containing even aromatic diamines as chain-extending agents show excellent stability in storage or, in casting systems, show greatly increased pot life, even when the polyamines in question are soluble and liquid aromatic polyamines.

In the case of one-component reactive mixtures, hardening may be carried out simply by heating in which case a rapid polyaddition reaction takes place above a certain temperature (the "thickening temperature"). It is possible, simply by varying the reaction conditions (for example, the temperature prevailing during the coating reaction), the choice of the liquid medium or the type and quantity of "amine stabilizers", to vary the "thickening temperature" and to adjust high stability in storage, even at relatively high storage temperatures.

The long-life, free-flowing, optionally readily meltable, heterogeneous one-component systems formed with the stabilized polyisocyanates may also be hardened by the addition of polar solvents (for example dimethyl formamide). In some cases, it is sufficient merely to apply intense shear forces.

In the case of thermal hardening, the one-component reactive polyurethane systems according to the invention may even be reacted at relatively low temperatures (above the thickening temperature, preferably ≧55° C. and, more preferably, in the range of from 100° to 135° C.). High-quality polyurethane plastics are thus obtainable depending on the reactants selected.

The findings according to the invention are surprising, were not apparent from the published literature and were not predictable by the expert. In addition, the polyurethanes (actually polyurethane "ureas") produced from the suspensions according to the invention based on relatively high molecular weight polyamines and/or aromatic, low molecular weight polyamines as chain-extending agents show improved properties such as higher moduli and higher softening ranges, by comparison with corresponding polyurethanes based on polyols.

The present invention thus relates to a process for the production of solid polyisocyanates stabilized by a polymer coating and showing retarded reactivity, comprising reacting (1) one or more solid polyisocyanates in particulate form having melting points above 30° C. and preferably above 80° C. (particle size preferably from 0.5 to 200 μm and most preferably 1 to 50 μm), with (2) from 0.1 to 25 equivalent percent (preferably in a quantity of from 0.1 to 8 equivalent percent and, most preferably, in a quantity of from 0.3 to 3 equivalent percent) of amine per isocyanate equivalent of an organic compound having a molecular weight of from 32 to 6000 (preferably from 60 to 3000), said organic compound being selected from the group consisting of (a) di- or higher functional (preferably difunctional to trifunctional and, most preferably difunctional) compounds containing two or more aliphatically bound, primary and/or secondary amino groups, (b) compounds containing one or more terminal —CO—NH—NH$_2$-groups, (c) hydrazines and (d) mixtures thereof, as "amine stabilizers", in the presence of (3) a liquid medium selected from the group consisting of (a) organic compounds containing one or more hydroxyl groups and having molecular weights of from 62 to 6000, (b) organic compounds containing two or more aromatically bound amino groups and having molecular weights of from 100 to 6000, (c) organic compounds containing two or more aliphatically bound amino groups and having molecular weights of from 400 to 6000, (d) plasticizers, (e) water, and (f) mixtures thereof. The liquid medium is preferably a relatively high molecular weight polyol and/or relatively high molecular weight aromatic and/or aliphatic polyamine having a molecular weight in the range from 400 to 6000, containing an addition of low molecular weight polyols (particularly diols and triols) and/or aromatic polyamines (preferably diamines) having molecular weights in the range from 60 to 399. The reaction may optionally be conducted in the presence of apolar or slightly polar solvents with boiling points below 146° C. preferably based on aliphatic cycloaliphatic or aromatic hydrocarbons, halogenated hydrocarbons, ethers, ketones and/or esters.

The reaction is conducted at a temperature below the melting temperature of the polyisocyanates, preferably at a temperature of up to about 70° C. and, more preferably, at a temperature in the range from 0° to 50° C. The resultant product is a suspension of polyadduct-coated, stabilized polyisocyanates in the liquid medium. If desired, the stabilized polyisocyanates may be isolated from any monoalcohols, plasticizers, water and/or solvents and then suspended in the polyols and/or polyamines.

In one preferred embodiment, the present invention relates to a process for the production of polyisocyanates stabilized by coating with a polyadduct using the procedure described above, characterized in that the solid polyisocyanates are reacted with hydrazine, alkyl hydrazines, N,N'-dialkyl-hydrazines containing C$_1$-C$_6$-alkyl groups and/or with difunctional or higher compounds containing terminal —CO.NH.NH$_2$-groups as "amine stabilizers" in a quantity of from 0.1 to 25 equivalent percent and preferably in a quantity of from 0.1 to 8 equivalent percent of a terminal hydrazine or hydrazide group per NCO-group in a liquid medium as in the process described above.

In yet another preferred embodiment the invention relates to a process for the production of polyisocyanates stabilized by a polymer coating using the procedures already described, characterized in that the solid polyisocyanates are reacted with the "amine stabilizers" in the quantities indicated in a liquid medium of relatively high molecular weight, aromatic and/or aliphatic polyamines having molecular weights in the range from 400 to 6000 and, optionally, in the presence of low molecular weight aromatic polyamines, low molecular weight and/or relatively high molecular weight polyols, plasticizers and/or water. The reaction may optionally be conducted in the presence of apolar or slightly polar solvents. The reaction is conducted at temperatures below the melting temperature of the polyisocyanates, to form a suspension of polyadduct-coated, stabilized polyisocyanates in the relatively high molecular weight polyamines. The stabilized polyisocyanates are optionally isolated (where the stabilization reaction is carried out in monoalcohols, plasticizers, water and/or slightly polar solvents) from the monoalcohols, plasticizers, water and/or slightly polar solvents and subsequently suspended in the relatively high molecular weight polyamines.

The most preferred procedure is that in which the polyisocyanates are directly reacted with the "amine stabilizers" in relatively high molecular weight polyols and/or relatively high molecular weight aromatic and/or aliphatic polyamines having molecular weights in the range from 400 to 6000, optionally in the presence of low molecular weight polyols and/or aromatic polyamines as chain-extending agents having molecular weights in the range from 60 to 399, to form the suspensions. The components are preferably reacted in quantities corresponding to a formulation for a one-component reactive polyurethane system.

The present invention also relates to polyadduct-coated, stabilized, solid, finely particulate polyisocyanates of retarded reactivity obtained by the processes according to the invention suspended in storable form in polyhydroxyl compounds (component (3)(a)) and/or in aromatic polyamines (component (3)(b)) and/or in aliphatic polyamines component (3)(c)). The preferred products are characterized by a residual NCO-content of from at least 75% (preferably from 92% and, more preferably from 97%) to less than 99.9% (and preferably less than 99.7%) of the NCO-groups originally present in the solid starting polyisocyanates and by a thickening temperature of the suspension of above 55° C., preferably in the range from 80° to 140° C. and, more preferably, in the range from 100° to 135° C.

The polyadduct-coated polyisocyanates are preferably suspended in a medium of polyols and/or aromatic and/or aliphatic polyamines having molecular weights of from 400 to 6000, optionally containing an addition of polyols and/or aromatic polyamines having molecular weights in the range from 62 to 399. Particularly preferred are polyadduct-coated polyisocyanates suspended in aromatic and/or aliphatic polyamines having molecular weights of from 400 to 6000 and preferably from 400 to 3000, optionally containing an addition of polyols (preferably diols and triols) and/or aromatic polyamines (preferably diamines) having a molecular weight in the range from 62 to 399 and, optionally, small quantities, based on the polyamines, of relatively high molecular weight polyols.

Also preferred are polyadduct-coated stabilized polyisocyanates, particularly using aliphatic polyamines as amine stabilizers, suspended in relatively high molecular weight polyols having molecular weights in the range from 400 to 6000 to which aromatic diamines and (optionally), low molecular weight polyols having a molecular weight of up to 399 have been added.

The present invention also relates to the use of polyadduct-coated, stabilized solid polyisocyanates of retarded reactivity obtained by the described processes in the form of suspensions in polyols (component 3(a)) and/or aromatic polyamino compounds (component 3(b)) and/or aliphatic polyamino compounds (component 3(c)). The suspensions, having the compositions indicated, serve as polyisocyanate component (A) and relatively high molecular weight polyol and/or polyamino compounds (B) and, optionally, low molecular weight chain-extending agents (C) for the production of polyurethanes, in preferably storable one-component systems comprising
  (A) polyisocyanates,
  (B) relatively high molecular weight polyhydroxyl and/or polyamino compounds,
  (C) optionally low molecular weight chain-extending agents,
  (D) optionally polyurethane catalysts and
  (E) optionally standard auxiliaries and additives.

The delayed-reaction polyisocyanates may be used both in the production of polyurethanes where the reaction time (pot life) is increased (for example in the case of casting systems). However, they may also be used in the production of one-component systems which remain stable for long periods at low temperatures and which are only reacted, for example, upon application of heat or by polar solvents.

More particularly, the present invention relates to the process for the production of polyurethanes from
  (A) polyisocyanates,
  (B) relatively high molecular weight polyhydroxyl and/or polyamino compounds,
  (C) optionally low molecular weight chain-extending agents,
  (D) optionally polyurethane catalysts and
  (E) optionally standard auxiliaries and additives, characterized in that the polyadduct-coated, suspended polyisocyanates obtained by the described processes are used as polyisocyanate component (A), relatively high molecular weight components (B) and, optionally, chain-extending agents (C). If desired, the suspended polyisocyanates may be used in combination with other non-stabilized polyisocyanates (A), relatively high molecular weight compounds (B) and chain-extending agents (C) and optionally using tertiary amine and/or metal catalysts (D) and auxiliaries (E). Free-flowing or readily meltable reactive polyurethane systems having a thickening temperature of $\geq 55°$ C. and the reactive polyurethane systems thus produced can be hardened by heat, shear forces and/or polar solvents to form solid or cellular polyurethanes.

In one preferred application, polyisocyanates stabilized in accordance with the invention with hydrazine, alkyl hydrazines, N,N'-dialkyl hydrazines (containing $C_1$–$C_6$-alkyl groups) and/or with di- or higher functional compounds containing terminal —CO—NH—$NH_2$-groups and having molecular weights of from 32 to 6000 or mixtures thereof and suspended in polyols (component 3(a)) and/or aromatic (component 3(b)) and/or aliphatic polyamines (component 3(c)) having molecular weights in the range from 400 to 6000, optionally in combination with polyols and/or aromatic polyamines having molecular weights in the range from 62 to 399, are used for the production of polyurethanes under the conditions described above.

In one particularly preferred application for the production of polyurethane-(ureas), the polyisocyanates stabilized by the above-mentioned "amine stabilizers" are used in the form of a suspension in a relatively high molecular weight aromatic and/or aliphatic polyamine, optionally containing an addition of low molecular weight aromatic polyamines, preferably diamines, and optionally low molecular weight polyols having molecular weights in the range from 62 to 399. In this case, no catalysts are required for hardening to form the polyurethane (urea). The temperatures and hardening times are effectively lower and shorter than in the case of polyol systems. Very favorable elastomer properties are also obtained.

In another preferred application for the production of polyurethanes, polyisocyanates obtained by the above-described processes and stabilized with "amine stabilizers", more particularly with difunctional or higher (preferably difunctional or trifunctional) compounds containing aliphatically bound primary and/or secondary amino groups and having molecular weights of from 60 to 3000 are used in the form of suspensions in relatively high molecular weight polyols (B) with aromatic polyamines as chain-extending agents (C). The aromatic polyamines are either used in the preparation of the suspension or are subsequently added as chain-extending agent to the polyurethane-forming reactive mixture. A mixture such as this may additionally contain low molecular weight polyols as chain-extending agents. In the case of using co-chain-extenders, at least 10 mole percent and preferably at least 50 mole percent of the chain-extending agents (C) are aromatic polyamines (preferably diamines). These systems are also characterized by favorable hardening behavior and, when compared to systems containing only polyol chain-extending agents, by better elastomer properties, such as, for example, strengths, mechanical properties and softening ranges.

The polyadduct-coated, stabilized polyisocyanates of retarded activity are preferably used as sole polyisocyanates (A) in the synthesis of polyurethanes. However, it is also possible to use combinations of the stabilized polyisocyanates and non-stabilized polyisocyanates, for example tolylene diisocyanates, diphenylmethane diisocyanates, naphthylene-1,5-diisocyanate or dimeric tolylene diisocyanate. In these combinations, however, the polyisocyanates stabilized in accordance with the invention are preferably used in a quantity of at least 50 equivalent percent.

Suitable non-stabilized polyisocyanates are any of the polyisocyanates described in German Offenlegungsschrift No. 29 20 501 (pages 12 to 16).

In cases where suspensions of the stabilized polyisocyanates in polyhydroxy and/or polyamino compounds (B) are used, the quantities of (B) may be selected in such a way that the composition corresponds exactly to the required polyurethane-forming component mixture (i.e., a "one-component reactive mixture"). However, if the composition of the polyurethane-forming mixture is different, additional components (B) (which may be the same or different) may be used for polyurethane production.

Similarly, the polyol or aromatic polyamine chain-extending agents (C) may optionally be used for the stabilization reaction in quantities suitable for one-component systems. Alternatively, component (C) may be added as additional chain-extending component.

In one embodiment, for example, the suspension of stabilized polyisocyanates in the relatively high molecular weight compounds (B) and, optionally, the low molecular weight compounds (C) is prepared in such a way that an excess of hydroxyl and/or amino groups is present in the suspension. The suspension may then be reacted with a normal (i.e. uncoated) polyisocyanate in such a way that all the hydroxyl and/or amino groups are able to react in substantially equivalent quantities with isocyanate groups from both the stabilized and non-stabilized polyisocyanates.

If the suspension of stabilized polyisocyanates in the relatively high molecular weight compounds (B) and, optionally, the chain-extending agents (C) contains an excess of isocyanate groups (from the coated polyisocyanates according to the invention), other relatively high molecular weight compounds (B) or low molecular weight compounds (C) may be added to the reaction mixture, followed by reaction to form the polyurethane. This may be done, for example, by separately metering and mixing the polyisocyanate suspension and the other components and then thermally hardening the resulting mixture, for example in a mold.

A preliminary decision as to whether a combination of a solid diisocyanate with an "amine stabilizer" is suitable for the production of storable one-component reactive polyurethane systems may be made on the basis of the following test to determine the "thickening temperature":

"DETA-test" for characterizing the coated polyisocyanates ("thickening temperature"):

1 mole of the solid diisocyanate modified with the "amine stabilizer" is suspended in 1000 g of a linear polyoxypropylene ether diol having a molecular weight of 2000. Following the addition of 0.5 mole of a 2,4-/2,6-(65/35) diamino-3,5-diethyltoluene isomer mixture (DETA), the one-component reactive mixture suspension is heated at a rate of approximately 10° C. per minute. The temperature at which the mixture rapidly assumes a paste-like consistency and ultimately solidifies is termed the "thickening temperature". Experience has shown that a thickening temperature below 55° C. indicates that a particular combination of solid polyisocyanates and amine stabilizer in the concentration in question is not really suitable for use in longlife, one-component reactive polyurethane systems, although, in the case of casting systems, for example, it may lead to a desired increase in the casting time. Polyurea-coated, amine-stabilized polyisocyanates of retarded reactivity which show thickening temperatures below 55° C. in the DETA-test have also been found by experience to be unsuitable for the preparation of storable one-component systems even where relatively high molecular weight polyamines are used as liquid medium in place of the diol used in the DETA-test.

Suitable starting components for the solid polyisocyanates stabilized in accordance with the invention include (1) any diisocyanates or polyisocyanates or mixtures thereof providing they have a melting point above 30° C., preferably above 40° C. and, more preferably, above 80° C. Such compounds include aliphatic, cycloaliphatic, araliphatic, and preferably aromatic and heterocyclic polyisocyanates. Specific examples include polyphenyl polymethylene polyisocyanates obtained by phosgenating aniline-formaldehyde condensates, as described in British Pat. Nos. 874,430 and 848,671; perchlorinated aryl polyisocyanates; polyisocyanates containing carbodiimide groups; polyisocyanates containing allophanate groups; polyisocyanates containing isocyanurate groups; polyisocyanates containing urethane or urea groups; polyisocyanates containing acylated urea groups; polyisocyanates containing biuret groups; polyisocyanates produced by telomerization reactions; polyisocyanates containing esters groups; diisocyanates preferably containing uret dione groups and diisocyanates containing urea groups. The following are mentioned as specific polyisocyanates which may be used in accordance with the invention:

|  | Melting Point |
|---|---|
| p-xylylene diisocyanate | 45–46° C. |
| 1,5-diisocyanato-methyl naphthalene | 88–89° C. |
| 1,3-phenylene diisocyanate | 51° C. |
| 1,4-phenylene diisocyanate | 94–96° C. |
| 1-methylbenzene-2,5-diisocyanate | 39° C. |
| 1,3-dimethylbenzene-4,6-diisocyanate | 70–71° C. |
| 1,4-dimethylbenzene-2,5-diisocyanate | 76° C. |
| 1-nitrobenzene-2,5-diisocyanate | 59–61° C. |
| 1,4-dichlorobenzene-2,5-diisocyanate | 134–137° C. |
| 1-methoxybenzene-2,4-diisocyanate | 75° C. |
| 1-methoxybenzene-2,5-diisocyanate | 89° C. |
| 1,3-dimethoxybenzene-4,6-diisocyanate | 125° C. |
| Azobenzene-4,4'-diisocyanate | 158–161° C. |
| Diphenylether-4,4'-diisocyanate | 66–68° C. |
| Diphenylmethane-4,4'-diisocyanate | 42° C. |
| Diphenyldimethylmethane-4,4'-diisocyanate | 92° C. |
| Naphthalene-1,5-diisocyanate | 130–132° C. |
| 3,3'-dimethylbiphenyl-4,4'-diisocyanate | 68–69° C. |
| Diphenyl disulfide-4,4'-diisocyanate | 58–60° C. |
| Diphenyl sulfone-4,4'-diisocyanate | 154° C. |
| 1-methylbenzene-2,4,6-triisocyanate | 75° C. |
| 1,3,5-trimethylbenzene-2,4,6-triisocyanate | 93° C. |
| Triphenyl methane-4,4',4Δ-triisocyanate | 89–90° C. |
| 4,4'-diisocyanato-(1,2)-diphenylethane | 88–90° C. |
| Dimeric-1-methyl-2,4-phenylene diisocyanate | 156° C. |
| Dimeric-1-isopropyl-2,4-phenylene diisocyanate | 125° C. |
| Dimeric-1-chloro-2,4-phenylene diisocyanate | 177° C. |
| Dimeric-2,4'-diisocyanato-diphenylsulfide | 178–180° C. |
| Dimeric-diphenylmethane-4,4'-diisocyanate | |
| 3,3'-diisocyanato-4,4'-dimethyl-N,N'—diphenyl urea | |
| N,N'—bis-[4-(4-isocyanatophenylmethyl)-phenyl]-urea | |
| N,N'—bis-[4-(2-isocyanatophenylmethyl)-phenyl]-urea. | |

According to the invention, it is particularly preferred to use 1,5-naphthalene diisocyanate, 3,3'-diisocyanato-4,4'-dimethyl-N,N'-diphenylurea, dimeric 1-methyl-2,4-diisocyanatobenzene, dimeric 4,4'-diisocyanatodiphenylmethane and 3,3'-dimethyl-4,4'-diisocyanatodiphenyl. The dimeric diisocyanates may also be produced in finely divided form by "in situ" dimerization, for example in plasticizers, solvents, water or polyols, and may optionally be subjected in that form to the amine stabilization reaction.

The "amine stabilizers" used for the above-mentioned polyisocyanates include component 2(a) which is a di-functional or higher, low molecular weight or relatively high molecular weight compound containing aliphatically bound primary and/or secondary amino groups and having molecular weights of from 60 to about 6000 and preferably from 60 to 3000. The compounds in question are low molecular weight and/or relatively high molecular weight primary and/or secondary polyamines, preferably diamines. As used herein, the term "aliphatically-bound" amine groups is meant to include amino groups attached to aliphatic groups (including cycloaliphatic groups) or to the aliphatic residue of araliphatic groups or in non-aromatic heterocyclic rings. In addition to the amino groups, the aliphatically-bound di- and polyamines may also contain OH-groups, tertiary amino groups, ether groups, thioether groups, urethane groups, urea groups, carboxyl groups or carboxylic acid alkylester groups.

Diamines and polyamines suitable for use in accordance with the invention include, for example, ethylene diamine; 1,2- and 1,3-propane diamine; 1,4-butane diamine; 1,6-hexane diamine; neopentane diamine; 2,2,4- and 2,4,4-trimethyl-1,6-diaminohexane; 2,5-dimethyl-2,5-diaminohexane; 1,10-decane diamine; 1,11-undecane diamine; 1,12-dodecane diamine; bisaminomethylhexahydro-4,7-methano-indane (TCD-diamine); 1,3-cyclohexane diamine; 1,4-cyclohexane diamine, 1-amino-3,3,5-trimethyl-5-amino-methyl cyclohexane (isophorone diamine); 2,4- and/or 2,6-hexahydrotolylene diamine; 2,4'- and 4,4'-diaminodicyclohexyl methane; m- or p-xylylene diamine; bis-(3-amino-propyl)methylamine; bis-N,N'-(3-aminopropyl)-piperazine; diaminoperhydroanthracenes; 1-amino-2-aminomethyl-3,3,5-(3,5,5)-trimethylcyclopentane; 2,2-dialkylpentane-1,5-diamines; triamines, such as 1,5,11-triaminoundecane; 4-aminomethyl-1,8-diaminooctane; lysine methyl ester and cycloaliphatic triamines as described in German Offenlegungsschrift No. 26 14 244; 4,7-dioxadecane-1,10-diamine; 2,4- and 2,6-diamino-3,5-diethyl-1-methylcyclohexane and mixtures thereof; alkylated diaminodicyclohexylmethanes, for example 3,3'-dimethyl-4,4'-diaminodicyclohexylmethane or 3,5-diisopropyl-3',5'-diethyl-4,4'-diaminodicyclohexylmethane; perhydrogenated diaminonaphthalenes; perhydrogenated diaminoanthracenes; higher amines, such as diethylene triamine, triethylene tetramine, pentaethylene hexamine, dipropylene triamine and tripropylene tetramine; N,N'-dimethyl ethylene diamine, 2,5-dimethyl piperazine; 2-methyl piperazine; piperazine (hydrate); and 2-hydroxyethyl piperazine.

In addition to or in admixture with these relatively low molecular weight aliphatic diamines (by "relatively low molecular weight" compounds containing aliphatically-bound amino groups, is meant molecular weights of less than 400) it is also possible to use relatively high molecular weight aliphatic di- and polyamines (i.e., molecular weights of 400 or more) of the type obtainable, for example by the reductive amination of polyoxyalkylene glycols with ammonia in accordance with Belgian Pat. No. 634,741 or U.S. Pat. No. 3,654,370. Other relatively high molecular weight polyoxyalkylene polyamines may be obtained by methods of the type described in the Company Publication entitled "Jeffamine, Polyoxypropylene Amines" by the Texaco Chemical Co., 1978; by the hydrogenation of cyanoethylated polyoxypropylene glycols (German Offenlegungsschrift No. 11 93 671); by the amination of polypropylene glycol sulfonic acid esters (U.S. Pat. No. 3,236,895), by the treatment of a polyoxyalkylene glycol with epichlorohydrin and a primary amine (French Pat. No. 1,466,708); or by the reaction of NCO-prepolymers with enamines, aldimines or ketimines containing hydroxyl groups, followed by hydrolysis in accordance with German Auslegeschrift No. 25 46 536. Other suitable relatively high molecular weight aliphatic di- and polyamines are the polyamines obtainable in accordance with German Offenlegungsschriften Nos. 29 48 419 and 30 39 600 by the alkaline hydrolysis of NCO-prepolymers (with aliphatic diisocyanates) with bases via the carbamate stage. These relatively high molecular weight polyamines have molecular weights of from about 400 to 6000, preferably from 400 to 3000 and, more preferably, from 1000 to 3000. By virtue of their structure, relatively high molecular weight polyamines such as these are particularly suitable for the formation of a non-fragile "elastic" polyurea coating. They may be used alone or in admixture with low molecular weight di- and polyamino compounds, for the amine stabilization of the polyisocyanate particles. Where these relatively high molecular weight amino compounds are used alone, there is no need to add any additional liquid medium (such as polyols) during the stabilization reaction (to "elasticize" the coating skin around the isocyanate particles). Some of these higher molecular weight polyamines may contain minor amounts of hydroxyl groups because of incomplete conversion of the OH groups into amine groups during the reductive amination step. As will be explained, such amine compounds (with or without hydroxyl groups) act both as an amine stabilizer and as the liquid medium.

Hydrazine, alkyl hydrazines and N,N'-dialkyl hydrazines, preferably containing $C_1$–$C_6$-alkyl groups, which may also contain chlorine or OH-groups as further substituents and having molecular weights of from 32 to 6000, and preferably from 32 to 198 may be used as the amine stabilizer. As noted earlier, difunctional or higher organic compounds containing terminal —CO.NH.NH$_2$-groups and having molecular weights of from 90 to about 6000 and preferably from 90 to 3000, are also used as "amine stabilizers" for the above-mentioned polyisocyanates. Examples of suitable stabilizers of these types include, for example, hydrazine (generally in the form of hydrazine hydrate), alkyl-substituted hydrazines, such as, for example, methyl hydrazine, ethyl hydrazine, hydroxy ethyl hydrazine or N,N'-dimethyl hydrazine. Other suitable "stabilizers" are compounds containing terminal hydrazide groups, such as di- and polyhydrazides, such as carbodihydrazide, hydracrylic acid hydrazide, oxalic acid dihydrazide, adipic ac dihydrazide, terephthalic acid dihydrazide and isophthalic acid hydrazide; compounds containing hydrazide and semicarbazide, carbazinic ester or amino groups, such as, for example, β-semicarbazidopropionic acid hydrazide, 2-semicarbazidoethylene carbazinic ester, amino acetic acid hydrazide, and β-aminopropionic acid hydrazide; bis-carbazinic esters or bis-semicarbazides, such as ethylene-bis-carbazinic ester and ethylene-bis-semicarbazide or isophorone-bis-semicarbazide. Hydrazines and lower molecular weight compounds containing —CO—NH—NH$_2$-groups and having molecular weights of from 32 to 399 are preferred. Hydrazine hydrate, β-semicarbazidopropionic acid hydrazide, isophorone-bis-semicarbazide, and alkylene-bis-semicarbazides are particularly preferred.

It is, of course, possible to use combinations of the above-mentioned "amine stabilizers" in order, for example, to offset adverse secondary effects of a given amine by corresponding advantages of other amines (for example low molecular weight and relatively high molecular weight diamines used together) or to combine as many favorable secondary effects as possible. Suitable combinations are, for example, combinations of fast-reacting amines, such as ethylene diamine, with amines slowed down by steric hindrance or combinations of low molecular weight amines with high molecular weight amines, such as for example aliphatic aminopolyethers, or of polyamines with hydrazines or hydrazide derivatives. In one preferred embodiment, it is preferred to use hydrazine or hydrazide derivatives in combination with at most up to 50 mole percent of polyamines, based on the total quantity of "amine stabilizers" used.

The low molecular weight aliphatic polyamines (i.e., molecular weight below 400), all the hydrazines, and all the compounds containing terminal —CO—NH—NH$_2$-groups may, as noted, contain hydroxyl groups. Such materials include β-hydroxyethyl-ethylene diamine, β-hydroxyethyl-piperazine, and β-hydroxyethyl-hydrazine. These families of amine stabilizers will react essentially and preferentially through the amino groups (and hydrazine or hydrazide groups). These families of materials are not considered suitable as the liquid medium and can only be used (and will only function as) the amine stabilizer. Amine-group containing hydrazides also only will function as an amine stabilizer.

The "amine stabilizers" are used in a quantity of from 0.1 to 25 equivalent percent of amine per equivalent of isocyanate in the polyisocyanate, preferably in a quantity of from 0.1 to 8 equivalent percent and, more preferably, in a quantity of from 0.3 to 3 equivalent percent. Although higher equivalent percentages, for example 30 equivalent percent of amine per NCO, may also be used for the polyadduct coating, conversions as high as these excessively reduce the percentage of reactive isocyanate groups remaining where the stabilized isocyanates are to be used in one-component reactive polyurethane systems. In the case of hydrazine(s), an —NH$_2$ group (or in the case of alkyl hydrazine derivatives, an —NH-alkyl group) counts as one amine equivalent; in the case of "hydrazide" compounds, a —CO—NH—NH$_2$-group counts as one amine equivalent.

The reactions are carried out at temperatures below the melting temperature of the particular polyisocyanate and generally at temperatures below 70° C., preferably at temperatures in the range from 0° to 50° C.

Stabilization of the isocyanate solid at room temperature with respect to active hydrogen compounds generally takes place within a few minutes so that continuous operation is also possible.

One-component reactive polyurethane systems containing the stabilized polyisocyanates according to the invention must on the one hand show almost indefinite stability in storage at room temperature or at moderately elevated temperatures (for example, in the range from 50° to 60° C.) and, on the other hand, crosslink rapidly at temperatures above about 100° C. The requirements which the stabilized polyisocyanates must satisfy in practice can be controlled to a large extent both through the quantity and also through the chemical constitution of the amine stabilizers and the reaction conditions (concentration, temperature) under which the reaction is conducted. Except in the case of high molecular weight aliphatic amines, if a certain quantity of amine (from the stabilizer) amounting to about ≧25 equivalent percent of amine per equivalent of NCO, is exceeded during the stabilization reaction, unsatisfactory crosslinking may occur under the usual heating conditions (110° to 140° C.) where the stabilized polyisocyanates are used in reactive polyurethane systems. Accordingly, it is advisable in making up the required formulation initially to determine the optimal addition of the particular amine stabilizer, the hardening temperature and hardening time in order to give adequate stability in storage (for example, 14 days at 50° C.) of the one-component systems. In general, the stabilizing effect of low molecular weight compounds containing primary amine groups is stronger than that of compounds containing secondary amino groups. The stabilizing effect also increases with increasing functionality of the amines. Triamines generally show stronger effects than diamines. By contrast, amino compounds of relatively high molecular weight show weaker effects, although they may be combined with low molecular weight diamines to obtain a stronger effect.

In the process according to the invention, the "amine stabilization" of the solid polyisocyanates by coating with a polyadduct is carried out in a liquid medium which is not a solvent (or an effective solvent) for the solid polyisocyanates.

The liquid medium may consist of (i) organic compounds containing one or, preferably more hydroxyl groups and having molecular weights of from 62 to 6000, and/or (ii) organic compounds containing two or more aromatically bound amino groups and having molecular weights of from 108 to 6000 and/or (iii) organic compounds containing two or more aliphatically-bound amino groups and having molecular weights in the range from 400 to 6000. However, it is preferred to use relatively high molecular weight (i) polyols and/or (ii) aromatic polyamines and/or (iii) aliphatic polyamines, having molecular weights in the range from 400 to 6000, preferably in the range from 400 to 3000 and, more preferably, in the range from 1000 to 3000, optionally in conjunction with low molecular weight polyols and/or aromatic polyamines (i.e., molecular weights of less than 400).

Examples of useful monoalcohols include relatively low-chain alcohols, such as isohexadecanol, and, propoxylation products of monohydric alcohols, said propoxylated products having molecular weights of preferably, from 4000 to 6000, (for example propoxylation products of n-butanol). However, monoalcohols are less preferred because they cannot be directly further used as suspending agents for polyisocyanates in the synthesis of polyurethanes since they are chain terminators. Accordingly, when used they must first be removed in an additional step before the polymer-coated polyisocyanates are used in a polyurethane-forming reactive system.

Suitable low molecular weight polyols include, for example, 1,4-butane diol, 1,10-decane diol, tetra-(hydroxypropyl)-ethylene diamine or castor oil.

The preferred relatively high molecular weight polyols (i.e., molecular weights of from 400 to 6000) include for example, polyoxyalkylene polyols, such as polyoxytetramethylene glycols or ethoxylation and/or propoxylation products of low molecular weight diols, polyols, diamines and polyamines. Examples include propoxylated trimethylol propane, propoxylated ethylene diamine or linear or branched polypropylene glycol ethers which may contain ethylene oxide is statistical, block-like or terminal form. One embodiment for example is characterized by the use of difunctional or higher, relatively high molecular weight polyols, optionally in combination with low molecular weight polyols, as the liquid medium for suspending the stabilized polyisocyanates which, when used in the synthesis of polyurethanes, are directly employed as reactants containing hydroxyl groups. Accordingly, it is possible to use any of the relatively high molecular weight compounds containing OH-groups normally used for the synthesis of polyurethanes as the liquid medium, such as polyethers, polyacetals, polythioethers and even polyesters of the type described, for example, in German Offenlegungsschrift No. 29 20 501. Where the suspension of the stabilized polyisocyanates in the polyols is directly used for one-component polyurethane systems, the relatively high molecular weight polyols B may also contain corresponding quantities of low molecular weight polyols, preferably diols, and/or aromatic polyamines, preferably diamines which have molecular weights in the range from 108 to 399. In many cases, however, these chain-extending agents are subsequently added to the suspensions of the polyurea-coated polyisocyanates. The low molecular weight aromatic polyamines may also be added with particular advantage to the system (as chain-extending agents) for the production of corresponding one-component reactive polyurethane systems. The components are preferably reacted in quantities corresponding to the formulation of the one-component reactive polyurethane systems.

Suitable, relatively high molecular weight polyhydroxyl compounds, which may be used both as suspending medium for the polyisocyanates and also as further reactive components for polyurethane production, include difunctional or higher polyhydroxyl compounds containing from 2 to 8 and preferably from 2 to 4 hydroxyl groups and having molecular weights of from 400 to 6000. Polyhydroxyl compounds such as these include polyesters, polyethers, polythioethers, polyacetals, polycarbonates, polylactones or polyesteramides containing at least two hydroxyl groups and also polybutadiene compounds or mixtures thereof of the type known per se for the production of homogeneous, optionally cellular or foam-like polyurethanes. Polyethers and polyesters are particularly preferred.

The polyethers in question are known and are obtained, for example, by polymerizing tetrahydrofuran or epoxides, such as ethylene oxide, propylene oxide, butylene oxide, styrene oxide or epichlorohydrin, or by the addition of these epoxide compounds, preferably ethylene oxide or propylene oxide, optionally in admixture or successively, with starter components containing reactive hydrogen atoms, such as water, polyhydric alcohols, ammonia, polyfunctional amines or sugars.

The polyesters containing hydroxyl groups suitable for use in accordance with the invention are, for example, reaction products of polyhydric (preferably dihydric and, optionally, even trihydric and higher) alcohols with polybasic (preferably dibasic) polycarboxylic acids or their anhydrides or corresponding polycarboxylic acid esters of lower alcohols.

The polycarboxylic acids may be aliphatic, cycloaliphatic, aromatic, araliphatic and/or heterocyclic and may optionally be substituted (for example by halogen atoms) and/or unsaturated.

Examples of carboxylic acids such as these and their derivatives include adipic acid, sebacic acid, azelaic acid, didodecanoic acid, phthalic acid, isophthalic acid, tetrahydrophthalic acid anhydride, tetrachlorophthalic acid anhydride, endomethylene tetrahydrophthalic acid anhydride, glutaric acid anhydride, maleic acid anhydride, fumaric acid, dimerized and trimerized unsaturated fatty acids, terephthalic acid dimethyl ester and terephthalic acid bis-glycol ester. Examples of suitable polyhydric alcohols include ethylene glycol, 1,2- and 1,3-propane diol, 1,4- and 2,3-butane diol, 2,3-dibromobutene diol, 1,6-hexane diol, 1,10-decane diol, neopentyl glycol, 1,4-bis-hydroxymethyl cyclohexane, 2-methyl-1,3-propane diol, glycerol, trimethylol propane, 1,2,6-hexane triol, pentaerythritol, quinitol, mannitol and sorbitol, formitol or formose, methyl glycoside, and di- tri- tetra-ethylene glycols, -propylene glycols and -butylene glycols.

Polyesters of lactones (for example $\epsilon$-caprolactone) or of hydroxy carboxylic acids (for example, $\omega$-hydroxy caproic acid) may also be used, particularly when they contain additional components, such as diethylene glycol or 1,4-butane diol, to reduce their high crystallinity.

Suitable polyacetals include, for example, the compounds obtainable from glycols and formaldehyde.

Suitable polycarbonates containing hydroxyl groups are known and may be produced, for example, by reacting 1,3-propane diol, 1,4-butane diol and/or 1,6-hexane diol, di- tri- or tetra-ethylene glycol or thiodiglycol, with diaryl carbonates (for example diphenyl carbonate) or phosgene.

Polybutadienes containing terminal hydroxyl groups are also suitable for use in accordance with the invention because they give particularly elastic and hydrolysis-resistant products.

It is also possible to use polyhydroxyl compounds containing high molecular weight polyadducts and polycondensates or polymers in finely disperse or even dissolved form. Polyhydroxyl compounds such as these are obtained, for example, by carrying out polyaddition reactions (for example reactions between polyisocyanates and aminofunctional compounds) or polycondensation reactions (for example between formaldehyde and phenols and/or amines) in situ in the above-mentioned compounds containing hydroxyl groups. Polyhydroxyl compounds modified by vinyl polymers, of the type obtained, for example, by polymerizing styrene and acrylonitrile in the presence of polyethers or polycarbonate polyols, are also suitable for the process according to the invention.

Other representatives of the above-mentioned compounds suitable for use in accordance with the invention are known and described, for example, in High Polymers, Vol. XVI, "Polyurethanes, Chemistry and Technology" by Saunders-Frisch, Interscience Publishers, New York/London, Vol. I, 1962, pages 32 to 42 and pages 44 to 54 and Vol. II, 1964, pages 5 to 6 and 198 to 199, and also in Kunststoff-Handbuch, Vol. VII, Vieweg-Hochtlen, Carl-Hanser-Verlag, Munich, 1966, for example on pages 45 to 71, and in DE-A No. 28, 54 384. It is of course possible to use mixtures of the above-mentioned polyhydroxyl compounds.

Liquid or low-melting (50° C.) low molecular weight and/or relatively high molecular weight aromatic polyamines (i.e., molecular weights of from 108 to 6000) and/or relatively high molecular weight aliphatic polyamines (i.e., molecular weights of from 400 to 6000) are also useful as the liquid medium. Low molecular weight aromatic polyamines (i.e., molecular weights up to 399) are less preferred as sole liquid medium, with relatively high molecular weight polyamines being preferred.

According to the invention, the relatively high molecular weight polyamino compounds containing aromatic amino groups and having a molecular weight in the range from 400 to 6000 include, in particular, polyamino compounds of the type which may be obtained by the (preferably basic) hydrolysis of corresponding NCO-prepolymers based on relatively high molecular weight polyhydroxyl compounds and excess aromatic diisocyanates. Examples of this process are given in German Offenlegungsschriften Nos. 29 48 419, 30 39 600 and 31 12 118 and in European published application Nos. 61 627 A, 71 132 A and 71 139 A. The first of these also describes other conventional processes for the production of aromatic amino compounds having a relatively high molecular weight structure of the type suitable for use in the process according to the invention. The processes described are particularly concerned with polyether polyamines, but also with polyester, polyacetal, polythioether or polycaprolactone polyamines, preferably difunctional or trifunctional polyamines, which contain urethane groups (from the reaction of the corresponding relatively high molecular weight polyhydroxyl compounds with the excess polyisocyanates) and which carry the amino groups on the residue of the polyisocyanate. However, the aromatic, relatively high molecular weight polyamines may also be obtained by other methods, for example by reacting NCO-prepolymers with excess quantities of hydrazine, aminophenyl ethylamine or other diamines in accordance with German Auslegeschrift No. 16 94 152. French Patent No. 1,415,317 describes another method in which the NCO-prepolymers are converted with formic acid into the N-formyl derivatives, followed by hydrolysis. The reaction of NCO-prepolymers with sulfamic acid in accordance with German Auslegeschrift No. 11 55 907 also leads to relatively high molecular weight polyamines. In addition to amino groups (from aromatic polyisocyanates) attached to aromatic residues, it is also possible to produce relatively high molecular weight polyamino compounds attached to aliphatic residues (through aliphatic polyisocyanates).

These relatively high molecular weight polyamines (i.e., molecular weights of from 400 to 6000) which were earlier described as relatively high molecular weight "amine stabilizers" may be used both as the "amine stabilizer" and as the liquid medium in cases where the "stabilization reaction" is carried out at low or moderate temperatures, for example $\leq 70°$ C., preferably room temperature. In this case, the "stabilization reaction" surprisingly comes to a stop at a conversion of less than 25% of all the NCO-groups. However, if the temperature is increased to a suitable level, for example to 120° C., all the aliphatic amino groups react completely with the isocyanate groups. In this case, it is possible directly to obtain elastomers providing the ratio between NCO-groups and NCO-reactive groups (OH— and/or $NH_2$-groups) is in the polymer-forming range (i.e, is close to 1:1).

Plasticizers may also be used as the liquid medium. Suitable plasticizers include hydrocarbons, carbonic acid esters or ethers or phosphate esters with alcohols having 8 or more carbon atoms. Suitable specific plasticizers include for example phthalates, such as dioctyl, diisododecyl, dibenzyl, butyl benzyl phthalate, or phosphates, such as trioctyl phosphate. Hydrocarbons, such as so-called butadiene oils, or polyethers of relatively high molecular weight may also be used as the liquid medium. In this case, the finely powdered, solid isocyanate is generally stirred into a solution of the amine stabilizer in the plasticizer, preferably, at room temperature. If it is intended to use the stabilized isocyanates in this suspension, any other starting components required, such as, for example, relatively high molecular weight aromatic polyamines, may be added after stabilization of the polyisocyanate. However, these plasticizers may also be used in admixture with the other disclosed liquid media as liquid medium for forming the suspension of the stabilized polyisocyanates. Isolation of the stabilized polyisocyanates from the plasticizers by filtration and the subsequent suspension in relatively high molecular weight polyol and/or polyamino compounds is also possible, although not preferred.

Surprisingly, water may also be used as the liquid medium, in which case the "amine stabilizers" are added to the water and the solid polyisocyanates mixed with the resulting solution. Where low molecular weight aliphatic polyamines in particular are used as amine stabilizers, however, completely satisfactory stabilization of the isocyanate is often only obtained if the process is carried out preferably in the presence of small quantities (for example from 2 to 25% by weight and preferably from 5 to 15% by weight, based on the amount of water) of a relatively high molecular weight polyol component or relatively high molecular weight polyamine component.

Where water is used as the principal liquid medium for stabilizing the polyisocyanates, the stabilized polyisocyanate is generally isolated by filtration, (optionally) dried and added in this isolated, finely powdered form to the required, relatively high molecular weight polyols and/or polyamines and, optionally, other starting components for the one-component reactive polyurethane mixtures. However, this intermediate stage of isolating the "stabilized" polyisocyanates is not preferred.

A polar or slightly polar solvents preferably with boiling points below 146° C., for example aliphatic, cycloaliphatic or aromatic hydrocarbons, halogenated hydrocarbons, ethers, ketones or esters, may optionally be added to the above-mentioned liquid media (polyols, polyamines, plasticizers or water). In this way, it is possible to obtain a reaction in a medium of lower viscosity. In this case, the solvents are preferably subsequently removed, for example, by distillation in vacuo.

The above-described stabilization reactions lead to a suspension of polyadduct-coated, stabilized polyisocyanates in the liquid medium.

The suspensions contain at least 3% by weight, preferably at least 5% by weight and, in most cases, at least 7% by weight of solid stabilized polyisocyanates. The solids contents are generally below 70% by weight, preferably below 50% by weight and, in most cases, below 40% by weight.

If the polyisocyanates are suspended in a medium which is suitable for the further reaction to form polyurethanes, as is the case for example with relatively high molecular weight polyols or polyamines, the suspension may be directly used as such. However, it is possible (although less preferred) to isolate the stabilized polyisocyanates from the suspension, for example by filtration, especially when water, monoalcohols or very large quantities of plasticizer and/or solvent are used, and to add them in powder form to the required polyurethane reaction components (the relatively high molecular weight polyols and/or polyamines and, optionally, low molecular weight chain-extending agents).

Particular significance is attributed to storable suspensions of the stabilized polyisocyanates in relatively high molecular weight polyamines, (optionally containing other relatively high molecular weight polyols and/or chain-extending agents, for example low molecular weight polyamines and low molecular weight polyols), which suspension may be directly used for the one-component reaction or for the formulation of one-component systems. The components are preferably blended in quantitative and equivalent ratios which directly correspond to the formulation of one-component reactive polyurethane systems.

The long-life one-component reactive polyurethane systems, which may be hardened to form solid or foamed polyurethanes, are preferably produced by in situ stabilization of the polyisocyanates using the amine stabilizers, in a liquid medium of one or more relatively high molecular weight polyols or polyamine compounds (which high molecular weight materials based required for the one-component polyurethane system) and, optionally, low molecular weight polyols and/or aromatic polyamines as chain-extending agents. To this end, a suitable "amine stabilizer" determined by preliminary tests is added in the required concentration to relatively high molecular weight polyols or polyamines, (for example to the polyhydroxy polyethers, polyesters or polycarbonates or to the amino polyethers, aminopolyesters or aminopolyacetals), preferably at as low a temperature as possible (room temperature). The particulate or powder-form polyisocyanate solid at room temperature is then added, the stabilized polyurea-coated polyisocyanate being formed within a few minutes. The required low molecular weight chain-extending agents, (C) preferably aromatic polyamines or low molecular weight (aliphatic or cycloaliphatic) polyol compounds, and optionally other relatively high molecular weight polyhydroxyl or polyamino compounds (B) and optionally the required catalyst (D) and the usual auxiliaries and additives (E) may be added to the suspension before or after the stabilizing reaction.

As already mentioned, the long-life one-component reactive systems according to the invention are preferably produced using low molecular weight chain-extending agents or crosslinking agents (component C) either as a part of the liquid medium or as a separately added component.

The low molecular weight chain-extending agents or crosslinking agents (component (C)) in question include difunctional or higher compounds containing hydroxyl groups attached to aliphatic and/or cycloaliphatic groups (polyols) and/or $NH_2$-groups attached to aromatic rings, including heterocyclic aromatic rings, (polyamines) and having molecular weights in the range from 62 to 399. Of these compounds, low molecular weight diols containing hydroxyl groups attached to aliphatic or cycloaliphatic groups and also aromatic diamines having molecular weights in the above-mentioned range (up to 399) are preferred.

These compounds generally contain from 2 to 8, preferably from 2 to 4 and, more preferably, 2 isocyanate-reactive hydrogen atoms, such as hydroxyl groups and/or amino groups. It is of course also possible to use mixtures of different compounds. Examples of such compounds include ethylene glycol, trimethylene glycol, 2,3-butane diol and/or 1,4-butane diol, 1,6-hexane diol, neopentyl glycol, 1,4-bis-hydroxyethyl cyclohexane, 1,4-dihydroxy cyclohexane, terephthalic acid-bis-($\beta$-hydroxyethyl)-ester, 1,4,3,6-dianhydrohexitols, 1,4-monoanhydrotetritols and, less preferably, diols containing secondary hydroxyl groups, such as propylene glycol, 2,3-butane diol or 2,5-pentane diol. Additional examples include trimethylol propane, trimethylol ethane, 1,2,6-hexane triol, glycerol, pentaerythritol, quinitol, mannitol, sorbitol, castor oil and also di-, tri- and tetraethylene, -propylene and -butylene glycols, bis-(2-hydroxyethyl)-hydroquinone, bis-(2-hydroxyethyl)-resorcinol, formose or formitol. Diols or polyols containing tertiary amines, for example N-methyl diethanolamine, triethanolamine or N,N'-bis-hydroxyethyl piperazine, are also suitable.

It is preferred to use low molecular weight aromatic diamines instead of low molecular weight polyols. Aromatic polyamines are also understood to be amines of the type which contain the amino group attached to heterocyclic radicals of aromatic character. Suitable aromatic polyamines include, for example, p-phenylene diamine; 2,4-/2,6-tolylene diamines; diphenylmethane-4,4'- and/or -2,4'- and/or -2,2'-diamines; 3,3'-dichloro-4,4'-diamino-diphenylmethane; 3-($C_1$–$C_8$)-alkyl-4,4'-diaminodiphenylmethanes, 3,3'-di-($C_1$–$C_4$)-4,4'-diaminodiphenylmethanes; and 3,3',5,5'-tetra-($C_1$–$C_4$)-alkyl-4,4'-diphenylmethanes; 4,4'-diaminodiphenyl sulfides, sulfoxides or sulfones; diamines containing ether groups as described in U.S. Pat. Nos. 3,654,364 and 3,736,295; 2-halogen-1,3-phenylene diamines optionally substituted in the 5-position as described in German Auslegeschriften Nos. 20 01 772, 20 25 896 and 20 65 869; bis-anthranilic acid esters as described in German Auslegeschriften Nos. 20 40 644 and 21 60 590; 2,4-diaminobenzoic acid esters according to German Auslegschrift No. 20 25 900; and, tolylene diamines substituted by one or two ($C_1$–$C_4$)-alkyl groups. Particularly preferred are 3,5-diethyl-2,4- and/or -2,6-diaminotoluene (and particularly their technical (80/20)- or (65/35)-isomer mixtures); asymmetrically tetraalkyl-substituted diaminodiphenyl methanes, for example 3,5-diethyl-3',5'-diisopropyl-4,4'-diaminodiphenylmethane, and isomer mixtures thereof according to German Auslegeschrift No. 29 02 090; 4,4'-diaminobenzanilide; 3,5-diaminobenzoic acid-($C_1$–$C_4$)-alkyl esters; 4,4'- and/or 2,4'-diaminodiphenylmethane; and naphthylene-1,5-diamine.

The aromatic diamines are preferred to the glycols. However, it is also possible to use diols or diamines containing additional groups, for example adipic acid-bis-(2-hydroxyethyl)-ester, terephthalic acid-bis-(2-hydroxyethyl)-ester, diol urethanes, diol ureas or polyols containing sulfonate and/or phosphonate groups, (for example, 1,6-hexamethylene-bis-(2-hydroxyethylurethane), 4,4'-diphenylmethane-bis-(2-hydroxyethylurea) or the adduct of sodium bisulfite with 1,4-butene diol or alkoxylation products thereof). Other useful low molecular weight compounds are described in detail in German Auslegeschrift No. 28 54 384.

In the polyurethane formulation, isocyanate-monofunctional compounds may optionally be used in the usual way as so-called chain terminators in quantities of from 0.01 to 10% by weight. Monofunctional compounds such as these include, for example, monoamines, such as butyl or dibutylamine, stearylamine, pyrrolidine, aniline or tolylamine, butanol, 2-ethyl hexanol, cyclohexanol or ethylene glycol monoethyl ester.

Suitable catalysts (D) for the long-life one-component systems according to the invention are the usual polyurethane catalysts, preferably organic lead and/or tin compounds, optionally in combination with other polyurethane catalysts, particularly those containing tertiary amines.

Of the lead compounds, compounds from the following groups are preferred:
(a) organic salts of divalent lead with carboxylic acid,
(b) dithiocarbamates of divalent lead corresponding to the following formula

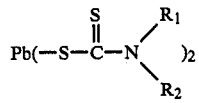

in which $R_1$ and $R_2$ may be the same or different and represent a $C_1$-$C_{20}$-alkyl radical,
(c) tetraorgano-lead-IV compounds, the organic radical being a lower alkyl radical, such as methyl or ethyl for example, and
(d) compounds of 1,3-dicarbonyl compounds, such as for example acetyl acetone, with divalent lead.

Suitable organo tin compounds include tin-(II) salts of carboxylic acids, such as tin acetate, tin octoate, tin ethyl hexanoate and tin laurate, and tin-(IV) compounds, such as dibutyl tin oxide, dibutyl tin dichloride, dibutyl tin diacetate, dibutyl tin dilaurate, dibutyl tin maleate or dibutyl tin diacetate.

Among the tin catalysts, however, it is preferred to use sulfur-containing tin compounds corresponding to the following formula

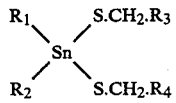

in which $R_1$ and $R_2$ represent $C_1$-$C_{10}$ alkyl radicals and $R_3$ and $R_4$ represent hydrogen and/or $C_1$-$C_{18}$-alkyl and/or the radical $COOR_1$.

Di-(octyl)-tin-(IV)-bis-thiomethyl or dimethyl-tin-bis-thiolauryl are mentioned as examples. Compounds in which $R_3$ and $R_4$ represent the above-mentioned ester radical, for example dimethyl-tin-bis-thioglycolic acid hexyl ester or dibutyl-tin-bis-thioglycolic acid octyl ester, are particularly preferred. The above-mentioned catalysts may of course be used in the form of mixtures, particularly when the low molecular weight chain-extending agents and the relatively high molecular weight polyols contain both primary and secondary OH-groups or when the NCO-reactive compounds have different reactivities.

Combinations of the organometallic compounds with amidines, aminopyridines, hydrazinopyridines (German Auslegeschriften Nos. 24 34 185, 26 01 082 and 26 03 834) or 1,4-diazabicyclo-2,2,2-octane and/or tertiary amine catalysts, of the type normally used in polyurethane chemistry, are also of interest.

The lead catalysts are characterized by particular activity and effectiveness when polyether polyols containing secondary hydroxyl groups, for example polypropylene oxide glycols, are used in the system.

In cases where uret dione diisocyanates are used, additional crosslinking may even occur through splitting of the uret dione ring, particularly where lead catalysts are used, although in that case branching allophanate groups or, if the uret dione ring is completely split, additional urethane groups are formed.

Where polyols containing predominant amounts of primary hydroxyl groups are used, however, the tin compounds, particularly the tin/sulfur catalysts, show good activity. Where polyethers containing amino groups are used, it is possible in some cases not to use any catalysts at all. The catalysts are generally used in quantities of from 0.001 to 5% by weight and preferably in quantities of from 0.01 to 2% by weight, based on (A) and (B).

Auxiliaries and additives (E) which may optionally be used in accordance with the invention include dyes or pigments; fillers, such as silica gel, gypsum, talcum, active carbon, metal powders; UV-absorbers or stabilizers, such as phenolic oxidation inhibitors; light stabilizers; blowing agents; surface-active additives, such as emulsifiers or foam stabilizers, cell regulators, antiblocking agents, silicones; flameproofing agents; or fungistatic and/or bacteriostatic agents.

Suitable fillers include, for example, fibrous materials, i.e. any inorganic and/or organic fibrous reinforcing materials, for example glass fibers, preferably in lengths of from 20 to 60 mm, graphite fibers and asbestos fibers or fibrous materials emanating from an organic polymer, for example from a polyester, such as polyethylene terephthalate, or preferably aromatic polyamines, such as m-phenylene/isophthalic acid polyamide or poly-p-phenylene terephthalamide, or even polycaprolactam. These fibrous materials may also be used in the form of mats, tows, full-length fibers, non-woven structures, woven structures or random staple-fiber mixtures. It is preferred to use glass fibers which have been treated with sizes to provide the fibers with an affinity for polyurethanes. The quantity of filler to be incorporated depends upon the required improvement in the mechanical properties and generally amounts to between 5 and 60% by weight.

In the polyurethane-forming reaction, the NCO/-(amine+OH)-ratio (NCO from reactive, unstabilized polyisocyanate and optionally other, free polyisocyanate to amino and/or OH-groups) amounts to between 0.5:1 and 1.5:1, preferably to between 0.8:1 and 1.5:1 and, more preferably, to between 0.95:1 and 1.2:1 (figures in equivalents).

From 0.3 to 10, preferably from 0.5 to 8 and, more preferably, from 0.75 to 5 equivalents of (OH+amine)-equivalents of chain-extending agents (C), i.e. low molecular weight polyols or low molecular weight polyamines, are preferably used per (OH+amine)-equivalent of relatively high molecular weight polyols and/or polyamines in the reactive polyurethane mixtures.

In general, dimeric diisocyanates containing uret dione rings may be regarded as diisocyanates so that only the free NCO-groups are taken into consideration. However, under certain experimental conditions (use of lead catalysts and relatively high processing temperatures, for example >140° C.), the uret dione ring enters into the reaction (additional linkage sites through allophanate or biuret groups), so that the latent NCO-groups of the uret dione ring must be taken into consideration in the calculation.

Depending on the viscosity or fusion behavior of the starting components, the one-component reactive polyurethane mixtures obtained can be readily pourable, knife-spreadable or solid at room temperature, or readily fusible. These reactive mixtures are a heterogeneous suspension of the solid, stabilized isocyanates in the polyol and/or polyamine components. The thermal crosslinking of this mixture is generally carried out after the addition of suitable catalysts (D). Without these catalysts, the polyurethane moldings obtained would have unsatisfactory properties, particularly where polyols are used as the relatively high molecular weight compounds (B) or chain-extending agents (C). However, there is no need whatever to use catalysts in cases where aromatic polyamine compounds which are distinctly more reactive to NCO-groups are used on their own.

Another feature of the one-component reactive polyurethane systems is that the one-component systems stabilized in accordance with the invention crosslink within a few minutes of reaching a certain temperature (depending on the type and quantity of stabilizing amine used). This means that, on the one hand, a desirable, long flow path of the as yet uncrosslinked reactive mixture enables a hot mold to be completely filled below that temperature ("thickening temperature"), while on the other hand the rapid solidification of the cast mixtures after an increase in temperature provides for rapid mold release cycles. Another advantage of the invention lies in the very long storage time of the starting reactive systems, even at relatively high storage temperatures (for example up to 60° C.). In this case, the advantage over the prior art, where a delay in the reaction of one-component systems is only obtained through the "heterogeneity" of one or more components, is additionally improved by the protective effect of the polyadduct coating which can only be eliminated by heat shock (or by high-intensity shear or by dissolution using highly polar solvents). The polyisocyanate suspensions according to the invention enable the range of potential applications of one-component systems to be considerably broadened. It is even possible to use liquid, not just solidifying, relatively high molecular weight polyamine and polyol systems and to select the chain-extending agents from a wider range (for example high-melting chain-extending agents).

An important feature of the one-component systems according to the invention lies in the fact that aromatic diamines (such as for example 4,4'-diaminodiphenylmethane, 2,4- or 2,6-diaminotoluene, 3,5-diethyl-2,4/2,6-(65/35)-diaminotoluene, 1,5-diaminonaphthalene or 3,5-diethyl-3',5'-diisopropyl-4,4'-diaminodiphenylmethane) may also be used as chain-extending agents without losing the character of a one-component system. If, by contrast, the diamines in question were to be reacted with NCO—prepolymers by one of the methods used hitherto, extremely short casting times would be the inevitable result, making it impossible to obtain satisfactory levelling of these mixtures in a mold.

By using relatively high molecular weight polyamines in the one-component systems, it is possible to obtain polyurethane (urea) (s) having distinctly more favorable properties (for example greater strengths, higher moduli, greater hardness and higher softening ranges) than those obtained when using relatively high molecular weight polyols alone or in the reactive polyurethane mixture.

The one-component systems (which may contain catalysts) according to the invention are preferably solidified by heat shock. Surprisingly, no crosslinking reaction takes place at room temperature or slightly elevated temperature, even in the presence of highly active catalysts, so that catalyst-containing mixtures may also be regarded as long-life one-component systems.

The processing of the one-component systems according to the invention is determined by their particular state. Liquid systems pourable at room temperature may be processed by casting. If necessary, they are briefly heated, for example to 50°-70° C., before processing. They may also be processed by centrifugal casting. Hollow bodies may be produced by introducing the reactive mixture into heated molds and distributing it over the surface of the molds by appropriate rotational movements. Heated molds may also be filled with the reactive mixture by the slush molding process. After a certain heating time/reaction on the heated surface of the mold, excess, unreacted reaction mixture is removed from the molds.

Where blowing agents are used, it is possible to produce cellular polyurethanes which may show an integral skin structure.

Non-pourable, but self-levelling systems may be applied, for example by means of a coating knife, to any desired substrates, for example, textile substrates such as nonwovens, woven and knitted fabrics, leather (skiver), matrices (for example velour leather/silicone matrices) or intermediate supports (for example separating papers), to form coatings or dressings, and subsequently hardened by application of heat.

Plastic systems (pastes) may be molded under pressure and heat, periods of only 5 to 15 minutes at 120° C. being sufficient for hardening.

Surface coatings, impression moldings or moldings may also be produced by dip coating, i.e., by immersing the heated molds to be coated in the reactive mixture.

The reactive mixture may also be extruded through slots or nozzles into hot media (hot air or hot liquids) and thereby solidified.

The reactive mixture can be partly or substantially completely reacted in heated extruders to form the polyurethane, extruded in that form through slots or nozzles and optionally reacted to completion in hot media. Alternatively, they may be introduced into hot molds from which they may be removed after a short time. The reacted mixture may also be processed by reaction injection molding (RIM).

Solid systems, particularly those based on relatively high melting starting polyols (45° to 65° C.), are processed either under pressure in molds (injection molding) or at or above the melting temperature of the polyol. In this case, the one-component systems produced beforehand may be introduced in the form of solid granulates into a mold heated to beyond the melting point of the polyol (generally below 70° C.). After the granulates with which the mold is filled have been melted, the mold is heated to between 100° and 120° C. and its contents solidified.

The solidification temperature of the one-component systems according to the invention depends to a large extent upon the quantity and chemical constitution of the amine stabilizers. The solidification time required for forming the polyurethanes decreases with increasing solidification temperature. The heating time may vary from less than 1 minute to several hours, depending on the temperature. In some cases, it is of advantage to temper the plastics for a while at 100° C. after they have been removed from the mold in order to guarantee complete hardening.

However, the one-component reactive systems may also be hardened by the addition of preferably highly polar solvents, such as dimethyl formamide, N-methyl pyrrolidone, or moderately polar solvents, such as propylene carbonate, dioxane or glycol monomethyl ether acetate. The stabilizing effect of the amine stabilizers on the polyisocyanates in the one-component systems may be partly or completely neutralized, depending on the quantity in which these solvents are used. The pouring time (pot life) of mixtures such as these may be controlled through the quantity in which solvents of the type in question are added. If the solvents are added in small quantities, the systems obtained have a pot life of several days at room temperature, whereas with larger additions rapid or even sudden solidification occurs after only 10 to 15 minutes. In this case, too, the quantities in which the above-mentioned solvents are used are governed by the type and quantity of the stabilizing amine (which determines the polyurea skin on the isocyanate surface) and are determined for the particular systems by preliminary tests. The technical advantage of reaction mixtures of this type lies in the fact that they solidify even in the absence of heat. The thermal solidification time of the one-component systems may of course also be reduced by suitably measuring the quantity of solvent added without any adverse effect upon their stability in storage.

The one-component systems according to the invention may also be solidified by the application of intense shear forces, for example in vessels equipped with high speed stirrers. In general, the heat effect generated by brief stirring is not sufficient to bring the one-component systems to the crosslinking-thickening temperature, so that the polyurea skin on the surface of the isocyanate particles is only destroyed by mechanical stressing during the stirring process.

Further embodiments of stabilization with amines under various conditions and processes for producing the one-component reactive systems and their hardening are described in the following Examples.

The reactive polyurethane systems preferably used are those which contain relatively high molecular weight polyamines (B) or chain-extending agents (C), (preferably low molecular weight aromatic polyamines) as components and which therefore give high-quality elastomers, coatings, cellular elastomers and moldings optionally having a density distribution characterized by a cellular inner core and a more compact outer skin.

EXAMPLES

EXAMPLE 1

"Stabilization" of dimeric tolylene-2,4-diisocyanate by sub-equivalent quantities of an amine stabilizer using various polyols or polyamines as suspension medium and stability of corresponding mixtures in storage.

The quantities indicated in Table 1 of "amine stabilizer" (aliphatic polyamines, hydrazine or "hydrazide" compounds) are dissolved in the polyol or polyamine component. 348 g (1 mole) of dimerized tolylene-2,4-diisocyanate (TT) in finely ground form (average particle size is $20 \pm 15$ μm) are suspended in the resulting solution in a high-speed mixer. Finally, the catalyst is added. In test 7 (using a polyether polyamine of relatively high molecular weight) no catalyst was used.

After degassing with stirring either at room temperature or at moderately elevated temperature (up to 50° C.), the reaction mixture is introduced into a cold or preheated casting mold and heated at 120° C. After a solidification time of a few minutes and a tempering time of approximately 1 hour, the cast mixtures are removed from the mold.

Storage tests were carried out in polyethylene bottles. The cast mixtures were regarded as stable if, after prolonged storage, they remain liquid and also hardenable at 120° C. (i.e., through reaction of the hitherto coated polyisocyanate components).

TABLE 1

| Test No. | Polyol component (g) | Amine stabilizer (g) | Equivalent % of stabilizer, based on TT | Hardening catalyst | Stability of the mixture Stabilized (according to the invention) at RT | 50° C. | Unstabilized (comparison) at RT | 50° C. |
|---|---|---|---|---|---|---|---|---|
| 1a | 2000 g of linear polypropylene glycol ether, MW = 2000 | 3.0 g of 2,5-diamino-2,5-dimethyl hexane | 2.0 | 0.2 g of Pb—octoate solution* | >3 Mon. | >3 Mon. | cross-linking in a few days | cross-linking in a few hours |
| 1b | 2000 g of linear polypropylene glycol ether, MW = 2000 | 6 g of 3,3'-dimethyl-4,4'-diaminodicyclohexyl methane | 2.5 | 0.2 g of Pb—octoate solution* | >3 Mon. | >3 Mon. | cross-linking in a few days | cross-linking in a few hours |
| 1c | 2000 g of linear polypropylene glycol ether, MW = 2000 | 1.9 g of 1,4-diaminocyclohexane | 1.7 | 0.2 g of Pb—octoate solution* | >3 Mon. | >3 Mon. | cross-linking in a few days | cross-linking in a few hours |
| 2 | 2000 g of linear propylene glycol ether containing 20% of terminal ethylene oxide groups, MW = 2000 | 9 g of 2,5-diamino-2,5-dimethyl hexane | 6.0 | 0.2 g of Pb—octoate solution* | >3 Mon. | >3 Mon. | cross-linking in a few days | cross-linking in a few hours |
| 3a | 2000 g of linear polyoxytetramethylene diol, MW = 2000 | 8 g of 2,5-diamino-2,5-dimethyl hexane | 5.3 | 0.2 g of Pb—octoate solution* | >3 Mon. | >3 Mon. | cross-linking in a few days | cross-linking in a few hours |
| 3b | 2000 g of linear polyoxytetramethylene diol, MW = 2000 | 8 g of 2,5-diamino-2,5-dimethyl hexane | 5.3 | 0.2 g of dioctyl tin-IV-di-(thioester)** | >3 Mon. | >3 Mon. | cross-linking in a few days | cross-linking in a few hours |
| 4 | 4000 g of trifunctional+ polypropylene polyethylene ether (80/20), | 3 g of 2,5-diamino-2,5-dimethyl hexane | 2.0 | 0.2 g of Pb—octoate solution* | >3 Mon. | >3 Mon. | cross-linking in a few | cross-linking in a few |

TABLE 1-continued

| Test No. | Polyol component (g) | Amine stabilizer (g) | Equivalent % of stabilizer, based on TT | Hardening catalyst | Stability of the mixture Stabilized (according to the invention) at RT | Stability of the mixture Stabilized (according to the invention) 50° C. | Stability of the mixture Unstabilized (comparison) at RT | Stability of the mixture Unstabilized (comparison) 50° C. |
|---|---|---|---|---|---|---|---|---|
| 5 | OH No. 28, MW = 6000 2600 g of dihydroxy polybutadiene, OH No. = 43, MW = 2600 (R45HT, a product of Metallges, Frankfurt on Main) | 3 g of 2,5-diamino-2,5-dimethyl hexane | 2.0 | 0.2 g of Pb—octoate solution* | >3 Mon. | >3 Mon. | days cross-linking in a few weeks | hours cross-linking in a few days |
| 6 | 2000 g of linear polyethylene glycol adipate MW = 2000 | 8 g of 2,5-dimethyl piperazine | 7.0 | 0.2 g of Pb—octoate solution* | >3 Mon. | >3 Mon. | cross-linking in 1-2 Mon. (inhibited by the solid state of the polyester) | cross-linking in a few hours |
| 7 | 2600 g of aromatic, relatively high molecular weight polyether polyamine, NH No. 43, of PPG-ether (OH No. 56) and tolylene-2,4-diisocyanate according to DE-OS No. 29 48 419 | 1.5 g of 2,5-diamino-2,5-dimethyl hexane | 1.0 | none | 3 Mon. | 3 Mon. | cross-linking after 1 hour | cross-linking in a few minutes |
| 8 | 2000 g of the linear polyether of Example 1/1 | 0.15 g of hydrazine hydrate | 3.0 | 0.2 g of Pb—octoate solution | 3 Mon. | 3 Mon. | cross-linking in about 1 hour | cross-linking in less than 1 hour |
| 9 | 2000 g of the linear polyether of Example 1/1 | 7.2 g β-aminopropionic acid hydrazide | 4.5 | 0.2 g of Pb—octoate solution | 3 Mon. | 3 Mon. | cross-linking in about 1 hour | cross-linking in less than 1 hour |

+started on trimethylol propane

TABLE 2
Mechanical properties of fully heated polyurethanes

| Example 1/Test No. | 1a | 1b | 1c | 2 | 3a | 3b | 4 | 5 | 6 | 7 | 8 | 9 |
|---|---|---|---|---|---|---|---|---|---|---|---|---|
| Tensile strength*** (DIN 53 504) [MPa] | 1.3 | 1.3 | 1.2 | 1.4 | 2.2 | 48 | — | 5.7 | 43 | 13 | 1.0 | 1.2 |
| Breaking elongation (DIN 53 504) [%] | 70 | 70 | 60 | 90 | 60 | 690 | — | 110 | 520 | 40 | 40 | 50 |
| Tear propagation resistance (DIN 53 515) [KN/m] | 2 | 2 | 1.9 | 1.6 | 4 | 21 | — | 11 | 10 | 40 | 1.6 | 1.7 |
| Shore hardness*** | | | | | | | | | | | | |
| (DIN 53 505) -A | 52 | 52 | 52 | 54 | 70 | 93 | — | 79 | 61 | 91 | 51 | 53 |
| -D | 11 | — | — | 17 | 24 | 29 | — | 28 | 27 | 36 | — | — |
| Elasticity*** (DIN 53 512) [%] | 53 | 53 | 54 | 52 | 67 | 66 | — | 59 | 50 | 56 | 50 | 54 |
| Compression set*** (DIN 53 517) after 24 h at 70° C. [%] | 59 | 60 | 60 | 13 | — | — | — | — | — | — | 62 | 58 |

*Both here and in the following Examples, the lead octoate solution is always a 57% solution of Pb—II-2-ethyl hexanoate in cleaning spirit (Octa-Soligen-Pb—24, a product of the Borchers Company, Dusseldorf)
**UI-29, a product of the Witco Company, USA
***In the following Examples, too, the values are determined in accordance with DIN Standards quoted.

EXAMPLE 2

"Thickening temperature" is dependent upon the type and quantity of "amine stabilizer" used.

The "thickening temperature" is defined as that temperature at which the mixture, when slowly heated (≃10° C./minute), assumes a paste-like consistency through the precipitation of hard segments attributable to a reaction between solid isocyanate and DETA.

The "thickening temperature" is dependent inter alia upon the type and quantity of amine stabilizer used and upon the type of polyisocyanate.

"Stabilized polyisocyanates" having a "thickening temperature" of at least 55° C. are preferred for one-component reactive polyurethane systems.

Experience has shown that lower "thickening temperatures" are indicative of inadequate "stabilization" of the polyisocyanate through coating with reaction products with the amine stabilizers when used for storable one-component systems.

If the quantity of amine stabilizer is too large, the polyisocyanates obtained, although having a higher "thickening temperature", do not show satisfactory hardening to form the finished polyurethane molding on account of the relatively high concentration of stabilizer.

"DETA-TEST"

Formulation 1 mole of linear polypropylene glycol ether, MW=2000,
X Eq.-% "amine stabilizer",
2 moles of dimeric, finely particulate tolylene diisocyanate ("TT"), average particles size 20±15 μm,
1 mole of 2,4-/2,6-diamino-3,5-diethyl toluene isomer mixture (65/35)—"DETA",
0.2 g of lead octoate solution per 100 g of polyol.

General Test Procedure

The "amine stabilizer" is dissolved in the polyol and the TT suspended in the resulting solution. After a reaction time of 30 minutes at room temperature, the DETA and the catalyst are added to the "stabilized" diisocyanate. The thickening temperature is determined as described above.

Instead of using TT, it is also possible to use other polyisocyanates melting at ≧30° C. Isolated, prestabilized polyisocyanates may also be used instead of amine stabilizer plus polyisocyanate.

TABLE 3

| Test No. | Type of "amine Stabilizer" | Quantity of stabilizer [Eq.-%], based on "TT" | | | |
|---|---|---|---|---|---|
| | | 0.5% | 1.0% | 1.5% | 3% |
| | | Thickening temperatures in °C. | | | |
| 1 | ethylene diamine | RT* | 60 | 80 | |
| 2 | diethylene triamine | " | | 90 | 150 |
| 3 | 2,5-diamino-2,5-dimethyl hexane | " | RT* | | 60 |
| 4 | neopentane diamine | " | | 80 | 130 |
| 5 | 1,6-diamino-2,4,4-trimethyl hexane | 80 | 105 | | 120 |
| 6 | bis-aminomethyl-hexahydro-4,7-methano-indane (TCD amine) | RT* | 85 | | 110 |
| 7 | isophorone diamine | " | | 70 | 85 |
| 8 | 2,4-diaminomethyl cyclohexane | " | | 70 | 90 |
| 9 | 4,4'-diaminodicyclo-hexylmethane | 75 | 85 | | 90 |
| 10 | 3,3'-dimethyl-4,4'-diaminodicyclohexyl methane | 70 | 70 | | 75 |
| 11 | 1,4-diaminocyclohexane | RT* | RT* | | 85 |
| 12 | 2-(2-aminoethylamino)-ethanol | " | | 75 | 115 |
| 13 | 1-amino-3-cyclohexyl aminopropane | 90 | 100 | | 105 |
| 14 | N,N'—dimethyl ethylene diamine | RT* | | 70 | 80 |
| 15 | 2,5-dimethyl piperazine | " | RT* | | 85 |
| 16 | triamino-polypropylene ether (Jeffamine T-403), MW = 438, a product of the Texaco Chemical Company, USA | 85 | 120 | | 130 |
| 17 | hydrazine (hydrate) | RT* | RT* | RT* | 60 |
| 18 | none (Comparison Test) | instantaneous thickening after the addition of DETA and crosslinking within one week at room temperature | | | |

*"Thickening at room temperature is indicative of an - in this case - inadequate "stabilizing effect"(coating reaction) of the "stabilizer"

EXAMPLE 3

Velocity of the coating reaction of a solid diisocyanate with different aliphatic diamines.

70 g of dimerized tolylene-2,4-diisocyanate (TT) are suspended in 200 g of a linear polypropylene glycol ether having a molecular weight of 2000. On the basis of prior experience, optimized quantities of aliphatic diamines (a)-(d) were stirred at room temperature into isocyanate suspensions prepared as described above for the "coating reaction" of TT. Samples are taken at certain intervals. After the substantially insoluble isocyanate has been separated off by filtration, the residual amine content in the filtrate is titrated with 0.1N HCl following the addition of acetone, water and phenol red.

TABLE 4

| Amine stabilizer | Eq. % | Residue of amine stabilizer in % of the starting quantity after x hours: | | | | | |
|---|---|---|---|---|---|---|---|
| | | x: 0.1 | 0.3 | 1 | 3 | 10 | 30 |
| (a) 0.6 g of 2,5-diamino-2,5-dimethyl hexane | 2.0 | 80 | 53 | 35 | 28 | 22 | 18 |
| (b) 0.2 g of ethylene diamine | 1.67 | 55 | 27 | 18 | 13 | 10 | 6 |
| (c) 0.34 g of relatively high molecular weight, trifunctional aliphatic polyamine (Jeffamine T-403, cf. Example 2, test No. 16) | 0.2 | 35 | 25 | 21 | 17 | 15 | 8 |
| (d) 1.2 g of 3,3'-dimethyl-4,4'-diamino-dicyclohexyl methane | 2.5 | 85 | 65 | 44 | 31 | 27 | 12 |

Accordingly, it can be seen that, even after a relatively long reaction time, there remains a certain residue of polyamine which is only able to further react very slowly in the reaction medium through the polyurea coating.

EXAMPLE 4

External production of coated polyisocyanates in organic solvents and subsequent use in one-component polyurethane reaction mixtures with aromatic diamine chain-extending agents.

50 g of TT are added in very finely powdered form to a solution of 0.5 g of ethylene diamine in 100 g of chlorobenzene, toluene or ligroin and the heterogeneous mixture stirred for one hour at room temperature. The isocyanate stabilized under these reaction conditions is then filtered off under suction, washed with the above solvent and carefully dried in vacuo.

34.8 g of this isocyanate are then suspended in 100 g of a linear polypropylene glycol ether (molecular weight 2000), followed by the addition of 8.9 g of a 2,4-/2,6-(65/35)-diamino-3,5-diethyl toluene isomer mixture and 0.2 g of lead octoate solution. In all three cases, there is a pronounced increase in viscosity at room temperature attributable to a preliminary reaction of the as yet inadequately stabilized (coated) isocyanates with the aromatic diamine (DETA). The reason for the inadequate stabilization could lie in an excessively fragile, inelastic coating provided by the polyurea formed.

However, if in addition to the aliphatic di- or polyamines various compounds are introduced in combination into the solvents, it is possible to obtain favorable stabilizing effects with these auxiliaries and aliphatic di- and polyamines. This could be attributable to an elasticizing effect of the auxiliaries which therefore provide for a more stable coating. The auxiliaries may be both compounds containing NCO-reactive groups, for example OH-functional polyethers or aromatic polyaminopolyethers, and also relatively high molecular weight, plasticizer-like compounds.

| Reaction mixture: |
| --- |
| 80 g of ligroin |
| x g of auxiliary |
| 0.5 g of ethylene diamine |
| 34.8 g of TT | are stirred for 1 hour at room temperature.

The "TT" thus stabilized is filtered under suction, dried and stirred into 100 parts of a polypropylene ether having a molecular weight of 2000 (linear structure). 8.9 g of DETA and 0.2 g of lead octoate solution are stirred into the resulting suspension.

TABLE 5

| Auxiliary x | Quantity (g) | Thickening point |
| --- | --- | --- |
| Polypropylene glycol ether, linear, MW 2000 | 15 | 130° C. |
| Polypropylene glycol ether, linear, MW 1000 | 15 | 128° C. |
| Aromatic aminopolyether, MW 2000, produced in accordance with DE-OS 2948419 | 15 | 138° C. |
| Tetrol of ethylene diamine and propylene oxide, OH number 630, MW 355 | 10 | 120° C. |
| Tetrol of ethylene diamine and propylene oxide, OH-number 470, MW 420 | 10 | 128° C. |
| Dioctyl phthalate (plasticizer) | 20 | 100° C. |

As the Examples show, an effective coating is formed around the isocyanate in the presence of the plasticizers or the co-reactants as auxiliaries.

If a relatively high molecular weight aliphatic amino polyether (Jeffamine D 2000, molecular weight 2000, according to U.S. Pat. No. 3,054,370) is used instead of ethylene diamine, a distinctly improved effect is observed (formation of a more elastic coating material). In most cases, it is necessary, in order to obtain a stabilizing effect comparable with that obtained by in situ stabilization within the actual polyol, to use a somewhat larger quantity of aliphatic, relatively high molecular weight polyamines of the type in question to obtain an adequate effect.

Instead of using the relatively high molecular weight Jeffamine, it is also possible to use combinations of (i) aliphatic low molecular weight amines and/or relatively high molecular weight aliphatic diamines and (ii) relatively high molecular weight polyols and/or aromatic polyamines, although in this case allowance must be made for the effect of the solvent (swelling or diffusion).

The following two Examples demonstrate this effect of solvents which is determined by the quality of the coating, i.e., by the type and quantity of the aliphatic diamines used (stabilizing effect).

| Mixture: |
| --- |
| 80 g of solvent (toluene or ligroin) |
| 15 g of linear polypropylene glycol ether, MW 2000 |
| 0.2 g of ethylene diamine |
| 34.8 g of TT/8.9 g of 2,4/2,6 (65/35)-diamino-2,5-diethyl toluene (DETA), |

| Mixture: |
| --- |
| 0.2 g of lead octoate solution. |

If the reaction is carried out in toluene as solvent, immediate thickening of the mixture is observed whereas the reaction mixture containing ligroin (the poorer solvent) is stable in storage.

EXAMPLE 5

External production of stabilized isocyanate General observation:

The external stabilization of an isocyanate with aliphatic polyamines may also be carried out in the presence of water providing the polyamine is used in combination with a low molecular weight and/or relatively high molecular weight polyol and/or low molecular weight or relatively high molecular weight aromatic polyamine. If the polyol or aromatic polyamine is not added, more amine stabilizer has to be used and this generally results in an excessive consumption of NCO.

Procedure 1.0 g of ethylene diamine (0.0167 moles/7 equivalent percent) is added to a solution of 20 g of a polyol having the constitution indicated in Table 6 in 100 ml of water. 50 g of 1,5-diisocyanatonaphthalene (0.238 mole; particle size 20–50 μm) are then added. No gas is given off during stirring for 1 to 2 hours at room temperature. The modified isocyanate is filtered off under suction and dried in vacuo.

21 g (0.1 mole) of the isocyanate thus modified are suspended in 100 g (0.05 mole) of a linear polypropylene glycol ether having a molecular weight of 2000, followed by the addition to the heterogeneous mixture of a solution of 0.2 g of lead octoate in 8.9 g (0.05 mole) of a 2,4-/2,6-(65/35)-diamino-3,5-diethyl toluene isomer mixture.

Whereas, in run No. 1 (in which no polyol is added), pronounced thickening is observed after a relatively short time (probably because of a "porous" layer of polyurea formed), the reaction mixtures according to the invention remain liquid and show the following thickening points (cf. Table 6).

TABLE 6

| | Polyol (20 g/100 g of H$_2$O) | Ethylene diamine (g) | Thickening point |
| --- | --- | --- | --- |
| 1 (a) | none (comparison) ("porous" polyurea-layer) | 1.0 | room temperature (approx. 2–3 mins.) |
| (b) | none | 3.0 | 56° C. |
| 2 | tetrol of ethylene diamine and propylene oxide, OH number 770, MW = 290 | 1.0 | 125° C. |
| 3 | triol of trimethylol propane and propylene oxide, OH number 850 | 1.0 | 105° C. |

EXAMPLE 6

Stabilization tests in various solvents (solvent/plasticizer/hydroxy compounds)

34.8 g (0.1 mole) of the uret dione diisocyanate (particle size 1 to 30 μm) produced by dimerization from 2,4-diisocyanatotoluene are added to a solution of 0.2 g of ethylene diamine (0.0033 mole; 3.3 equivalent percent) in quantities of 80 g of the solvents indicated below. The heterogeneous mixture is stirred for 30 to 60 minutes at room temperature.

The stabilized isocyanate suspension is mixed with 8.9 g (0.05 mole) of a 2,4-/2,6-(65/35)-diamino-3,5-diethyl toluene isomer mixture (DETA).

If stabilization is inadequate, i.e., if an incomplete or porous coating is formed around the isocyanate by the polyurea (from the reaction of isocyanate groups and ethylene diamine), a marked increase in viscosity occurs after a short time. A reaction mixture of paste-like consistency is obtained due to the preliminary reaction of the aromatic diamine with the diisocyanate (cf. Examples 1 to 8 in Table 7 which do not correspond to the invention).

By contrast, if the isocyanate is completely stabilized with respect to the aromatic amino groups, the reaction mixtures remain liquid and stable in storage for at least 3 months at room temperature or slightly elevated temperatures. The thickening temperature may be determined as a measure of the quality of "stabilization". If the "thickening point" is situated in a narrow temperature range, the isocyanates are destabilized (complete or partial destruction of the polyurea coating).

In order to measure the thickening temperature of the particular systems, 10 to 20 g samples of the particular mixtures were slowly heated until sudden thickening occurred. The higher the thickening point, the more stable the behavior of the isocyanate stabilized by the process according to the invention with respect to compounds containing groups carrying reactive hydrogen.

TABLE 7

|  | Solvent | Functionality (to NCO—groups) | Molecular weight | Thickening point °C. | |
| --- | --- | --- | --- | --- | --- |
| 1. | toluene | 0 |  | ≦room temperature | comparison |
| 2. | chlorobenzene | 0 |  | ≦room temperature | comparison |
| 3. | petroleum ether | 0 |  | ≦room temperature | comparison |
| 4. | ligroin | 0 |  | ≦room temperature | comparison |
| 5. | dioxane | 0 |  | ≦room temperature | comparison |
| 6. | methyl glycol ether acetate | 0 (b.p. 145° C.) |  | ≦room temperature | comparison |
| 7. | glycol dimethyl ether | 0 |  | ≦room temperature | comparison |
| 8. | phosphoric acid tributyl ester (too highly polar compound) | 0 |  | ≦room temperature | comparison |
| 9. | dioctyl phthalate (plasticizer) | 0 | 390 | 80 | according to invention |
| 10. | polybutadiene (Lithene PM (a product of ARCO/USA)) | 0 | 1000 | 110 | according to invention |
| 11. | ethylene glycol | 2 |  | 103 | according to invention |
| 12. | N—methyl diethanolamine | 2 |  | 82 | according to invention |
| 13. | isohexadecanol | 1 |  | 62 | according to invention |
| 14.+ | trimethylol propane reacted with propylene oxide to an OH number of 550 | 3 | 300 | 140 | according to the invention |
| 15.+ | ethylene diamine reacted with propylene oxide to an OH number of 470 | 4 | 480 | 130 | according to the invention |
| 16.+ | butanol reacted with propylene oxide | 1 | 1400 | 130 | according to the invention |
| 17.+ | butanol reacted with propylene oxide | 1 | 2000 | 130 | according to the invention |
| 18. | linear propylene glycol ether, 15% of terminal ethylene oxide groups, OH number 28 | 2 | 4000 | 140 | according to the invention |
| 19. | linear propylene glycol ether, 15% of terminal ethylene oxide groups, OH number 56 | 2 | 2000 | 143 | according to the invention |
| 20. | linear propylene glycol ether, 15% of terminal ethylene oxide groups, OH number 112 | 2 | 1000 | 130 | according to the invention |
| 21. | linear propylene glycol ether, 15% of terminal ethylene oxide groups, OH number 35 | 2 | 3200 | 135 | according to the invention |
| 22. | trifunctional polypropylene ether triol, OH number 28 | 3 | 6000 | 125 | according to the invention |
| 23. | castor oil | 3 | approx. 1000 | 115 | according to the invention |

TABLE 7-continued

| | Solvent | Functionality (to NCO—groups) | Molecular weight | Thickening point °C. | |
|---|---|---|---|---|---|
| 24. | polyethylene glycol ether | 2 | 400 | 105 | according to the invention |

+polyether, prepared from

The stabilization of the isocyanates by ethylene diamine is inadequate in solvents 1 to 8 because of the porous, fragile and swellable polyurea coating. Thickening in one-component polyurethane systems occurs shortly after addition of the aromatic diamine.

It is only in cases where the compounds used as plasticizers are relatively higher molecular weight compounds, preferably from the group comprising hydrocarbons, ethers or esters, carbonic acid esters, or phosphoric acid esters of alcohols having more than 8 carbon atoms, (for example plasticizer compounds 9 or 10) that a distinct stabilizing effect of the isocyanates is discernible (formation of an elastic, substantially indestructible polyurea coating). Of course, mono- or polyhydroxy compounds (for example compounds 11 to 23 in Table 7) may also be used as the liquid medium. Excessively polar plasticizers containing phosphoric acid ester groups show an overly strong dissolving effect and prevent effective "coating" of the polyisocyanates. However, if more amine stabilizer is used, an adequate coating is obtained, although an excessive NCO-loss is observed and the material becomes inhomogeneous and lumpy.

EXAMPLE 7

The use of stabilized polyisocyanates in one-component polyurethane formulations containing different aromatic diamines as chain-extending agents.

Formulation 1 mole of linear polypropylene glycol ether diol, molecular weight 2000, 0.02–0.03 mole of "amine stabilizer" (2,5-diamino-2,5-dimethyl hexane)
2 moles of dimeric tolylene diisocyanate (TT)
1 mole of aromatic diamine (see Table 8)
0.2 g of lead octoate solution per 100 g of polyol General Procedure 35 parts of dimeric tolylene diisocyanate are suspended in 40 parts of the polyol. After addition of the "amine stabilizer" in the quantity indicated in Table 8, the mixture is left to react for 30 minutes at room temperature, resulting in formation of the stabilized diisocyanate.

After addition of the aromatic amine dissolved and/or suspended in 60 parts of the polyol and the catalyst, the mixture is degassed with stirring at room temperature, introduced into a cold or slightly preheated casting mold and heated at 120° C. After a solidification time of a few minutes and tempering for 1 hour, the mixture is removed from the mold.

If they are not fully heated, the mixtures may be stored almost indefinitely (≧4 months) at temperatures of up to 50° C. If, by contrast, the unstabilized dimeric tolylene diisocyanate is used in the above formulation (without the aliphatic diamine stabilizer), thickening of the one-component polyurethane mixture occurs within a few minutes at room temperature, followed immediately by hardening.

TABLE 8

| | One-component polyurethane formulation and properties | | | | |
|---|---|---|---|---|---|
| Test No. | 1 | 2 | 3 | 4 | 5 |
| Aromat. diamine (as chain extender) | 2,4-/2,6-(65/35)-diamino-3,5-diethyl toluene isomer mixture | 2,4-diamino toluene | 4,4'-diamino-diphenyl methane | 3,5-diisopropyl-3',5'-diethyl-4,4'-diaminodi-phenylmethane | 1,5-diamino-naphthalene |
| Parts by weight of aromatic diamine | 8.9 | 6.1 | 9.9 | 16.9 | 7.9 |
| Aromatic diamine introduced in the form of a | solution | solution/suspension in 60 parts of polyol | solution | solution | solution |
| Parts of aliphatic amine stabilizer per 100 parts of polyol | 0.4 | 0.3 | 0.4 | 0.3 | 0.3 |
| Eq.-%, based on TT | 3 | 2.25 | 3 | 3.35 | 2.25 |
| Thickening temp. of the mixture in °C. | 68 | 85 | 93 | 85 | 95 |
| Temp. at which hardening (thickening) occurs in 1 minute [°C.] | 100 | 108 | 108 | 103 | 102 |
| Mechanical properties: | | | | | |
| Tensile strength [MPa] | 8.9 | 7.6 | 9.3 | 11.5 | 9.2 |
| Breaking elongation [%] | 150 | 140 | 110 | 260 | 160 |
| Tear propagation resistance [KN/m] | 11.0 | 12 | 11.4 | 15 | 9 |
| Shore hardness -A | 91 | 81 | 83 | 86 | 77 |
| -D | 34 | 29 | 31 | 32 | 26 |
| Elasticity [%] | 46 | 47 | 48 | 45 | 53 |

EXAMPLE 8

Stabilized polyester-based one-component polyurethane systems using various catalysts (A) 2 g (0.0175 mole) of 2,5-dimethyl piperazine (7 equivalent percent, based on NCO) are added to 500 g of a linear polyester diol of adipic acid and ethylene glycol (molecular weight 2000) melted at approximately 55° C. 87 g (0.25 mole) of dimeric 2,4-diisocyanatotoluene (TT) in the form of a finely ground powder (10-30 μm) and 1 g of a 50% lead octoate solution in petrol are then stirred in.

After brief degassing of the reaction mixture, the melt is poured into a mold and heated at 120° C. After a solidification time of a few minutes, followed by tempering for about 1 to 2 hours, a transparent highly elastic material having the mechanical properties set out in Table 9 is obtained.

(B) If 2.0 g of Fomrez UL 29 (an S-containing Sn-catalyst produced by the Witco Company, USA) are used instead of 2.0 g of lead octoate solution in test (A), a transparent, but distinctly more rigid molding having the properties set out in Table 9 is obtained under the same working conditions.

(C) If the polyester mentioned in Example 8, test (A) is replaced by a linear polyester of adipic acid and an ethylene glycol/1,4-butane diol (1:1) mixture (OH number 56), a molding having the mechanical properties set out in Table 9 is obtained under the same conditions as in (A).

(D) Catalysis using Fomrez UL 29 instead of lead octoate in formulation (C) also leads to a transparent, but distinctly more rigid elastomer.

TABLE 9

| Mechanical properties | A | B | C | D |
|---|---|---|---|---|
| Tensile strength [MPa] | 35 | 36 | 10.5 | 37 |
| Breaking elongation [%] | 470 | 780 | 334 | 860 |
| Tear propagation resistance [KN/m] | 11.3 | 52 | 7.5 | 45 |
| Shore hardness - A | 65 | 82 | 69 | 83 |
| - D | 18 | 29 | 21 | 28 |
| Elasticity [%] | 54 | 58 | 65 | 62 |

If, in tests (A) to (D), the reaction mixture is not directly heated to form the polyurethane, but instead is left to cool to around 55° to 60° C., storable one-component polyurethane systems are obtained in the form of solid granulates or highly viscous pastes.

These systems may be introduced after any length of time into a mold heated to approximately 70° to 100° C. After melting (60° to 80° C.), the now thinly liquid melt fills the mold, the flow characteristic being determined by the temperature of the mold. Final hardening takes place at a temperature in the range from 110° to 120° C.

Accordingly, these one-component systems may be processed by casting providing the processing temperature is above the melting temperature of the polyester. To this end, it is advisable to melt (50°-70° C.) and degas the storable reaction mixture before processing and then to introduce it into the required preheated molds, followed by heating at 110° to 120° C. After a solidification time of a few minutes, followed by tempering for 30 to 60 minutes, the highly elastic elastomers may be removed from the molds.

EXAMPLE 9

Test (A)

2.0 g (0.175 mole) of 2,5-dimethyl piperazine (4.66 Eq.-%) are added as "amine stabilizer" at around 50° to 70° C. to 500 g of a linear polyester of adipic acid and ethylene glycol having an OH-number of 56 (molecular weight 2000). 131 g (0.376 mole) of a uret dione diisocyanate based on 2,4-diisocyanatotoluene are then stirred into the mixture in the form of a finely ground powder (10-40 μm).

After stirring for a few minutes, 22.25 g (0.125 mole) of a 2,4-/2,6-(65/35)-diamino-3,5-diethyl toluene isomer mixture and 1 g of lead octoate solution are added to the stabilized diisocyanate suspension. After brief degassing of the reaction mixture, the melt is poured into a mold heated at 120° C. After a solidification time of a few minutes, followed by tempering for about 1 to 2 hours, a highly elastic material having the properties shown in Table 10 is obtained.

Test (B) (more rigid version)

2.5 g (0.022 mole) of 2,5-dimethyl piperazine (4.4 Eq.-%) are added as "amine stabilizer" to 500 g of the linear polyester used in test (A). 174 g (0.50 mole) of the uret dione diisocyanate of (A) are then stirred into the mixture in the form of a fine powder.

After stirring for a few minutes, 44.5 g (0.25 mole) of the aromatic diamine from test (A) and 1 g of the sulfur-containing tin-IV catalyst, UL-29 (a product of the Witco Company), are added to the stabilized polyisocyanate suspension. After brief degassing of the reaction mixture, the melt is poured into a mold and heated for 1.5 hours at 120° C., a highly elastic material being obtained (cf. Table 10).

If the test is repeated without any "amine stabilizer", thickening and crosslinking occur after only about 30 minutes at 50° C. in the presence of the catalyst. According to the invention, i.e., using an "amine stabilizer", the reaction mixture is virtually unchanged after 18 hours at 60° C. and, to initiate the polyurethane-forming reaction, has to be heated to 120° C.

TABLE 10

| Mechanical properties | | |
|---|---|---|
| Test No. | 9A | 9B |
| Tensile strength [MPa] | 40 | 34 |
| Breaking elongation [%] | 475 | 620 |
| Tear propagation resistance [KN/m] | 20.5 | 80 |
| Shore hardness - A | 81 | 92 |
| - D | 32 | 42 |
| Elasticity [%] | 40 | 48 |

EXAMPLE 10

"Stabilized" naphthylene diisocyanate and a corresponding one-component polyurethane reactive system:

General formulation 100 g (0.05 mole) of a linear polypropylene glycol diol, molecular weight 2000, x g of ethylene diamine, 21 g (0.01 mole) of naphthylene-1,5-diisocyanate (average particle size 20 μm±10 μm)

8.9 g (0.05 mole) of aromatic diamine (DETA) and 0.2 g of lead octoate solution.

The polyether diol to which different quantities (x) of ethylene diamine have been added is converted by addition of the diisocyanate into a stabilized diisocyanate suspension and subsequently mixed with the aromatic diamine and catalyst. The thickening points, as a function of the quantity of stabilizers, are shown in Table 11.

TABLE 11

Thickening points dependent upon the quantity of stabilizer.

| Ethylene diamine g/100 g of polyether | Eq. % | Thickening point (°C.) |
|---|---|---|
| 1.0 | 16.6 | 128 |
| 0.75 | 12.5 | 127 |
| 0.60 | 10.0 | 125 |
| 0.5 | 8.3 | 124 |
| 0.2 | 3.33 | room temperature (≈5 mins) |
| none | — | room temperature (≈1-3 mins) |

EXAMPLE 11

Stabilization of a urea diisocyanate and its use in one-component reactive polyurethane mixtures Formulation 50 g (0.025 mole) of a linear polypropylene oxide diol containing 20% of terminal ethylene oxide groups, molecular weight 2000

16 g (0.045 mole) of urea diisocyanate 50 g of an aromatic aminopolyether based on a polypropylene oxide ether diol and tolylene diisocyanate (see below)

0.4 g of N,N'-dimethyl ethylene diamine and 0.2 g of tin catalyst 50 g of the aminopolyether are added to and mixed with a suspension—in 50 g of the polypropylene oxide diol—of 16 g of 4,4'-diisocyanato-3,3'-dimethyl diphenyl urea (M.p. 180° C., urea diisocyanate/THDI) obtained from 2 moles of 2,4-diisocyanatotoluene and 1 mole of water in acetone solution. 0.4 g of N,N'-dimethyl ethylene diamine and 0.2 g of dibutyl tin-IV-2-ethyl hexanoate are then added. The resulting mixture is storable almost indefinitely at room temperature. An elastic molding having a shore-A-hardness of from 75 to 80 is obtained after heating from 30 to 60 minutes at 120° to 140° C.

In the absence of amine stabilization, the reaction mixture gradually thickens at room temperature.

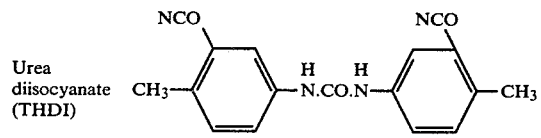

Urea diisocyanate (THDI)

Aminopolyether

Production was carried out in accordance with Example 2—method A—of German Offenlegungsschrift No. 30 39 600 by the alkali hydrolysis of a linear NCO-prepolymer of a linear polyoxypropylene ether diol (molecular weight 2000) and 2,4-tolylene diisocyanate (molar ratio 1:2) and carbamate decomposition using an acid ion exchanger. The aromatic polyamine has a molecular weight of 2400 and an NH-value of 41.5.

EXAMPLE 12

Stabilization of other diisocyanates

The quantities of stabilizing diamine (ethylene diamine) indicated below are added to 100 g of a linear polypropylene oxide diol (molecular weight 2000), followed by addition of the diisocyanates mentioned in the form of fine powders.

Low-melting diisocyanates (for example 4,4'-diisocyanato-diphenyl methane—M.p. 40° C.—or other diisocyanates, for example 1,4-diisocyanatobenzene (M.p. 95° C.)) may also be converted into fine powders by melting the corresponding isocyanates (100 g) and rapidly introducing the resulting melt into cold (0°–4° C.) petroleum ether (300 g) with intensive stirring. The solid isocyanates are precipitated in the form of a uniformly fine powder.

After the polypropylene oxide ether has been mixed with ethylene diamine and one of the diisocyanates indicated, 0.2 g of lead octoate solution and 8.9 g of the aromatic diamine (DETA) are added to the stabilized suspension and the thickening point of the reactive mixtures thus produced is determined (see Table 12). Without stabilization, rapid thickening occurs, resulting in the formation of a paste which can no longer be processed.

TABLE 12

| Diisocyanate | Ethylene diamine (g/100 g of PE) | Thickening point (C.°) |
|---|---|---|
| 1. 4,4'-diisocyanato-3,3'-dimethyl diphenyl urea | 0.2 | 142 |
| 2. 1,4-diisocyanatobenzene | 0.6 | 125 |
| 3. 4,4'-diisocyanato-diphenyl methane | 0.8 | 95 |

EXAMPLE 13

The use of stabilized diisocyanates in polyol-crosslinked reactive polyurethane systems Test (A): Crosslinking with polyols 31.5 g (0.15 mole) of finely powdered 1,5-diisocyanato-naphthalene (average particle size 20±10 μm) are added to a solution of 0.5 g of ethylene diamine in 100 g (0.05 mole) of a linear polypropylene oxide ether diol (molecular weight 2000). 0.1 mole of the low molecular weight polyols indicated below in Table 13 and 0.2 g of lead octoate solution are then added to the stabilized diisocyanate suspension. If the isocyanate is not stabilized or inadequately stabilized, rapid thickening occurs, whereas the reaction mixtures according to the invention remain liquid and storable at room temperature and show relatively high thickening points (see Table 13).

TABLE 13

| Polyol (0.1 mole) | Quantity (g) | Thickening point (°C.) |
|---|---|---|
| 1. ethylene glycol | 6.2 | 92 |
| 2. 1,4-butane diol | 9.0 | 105 |
| 3. diethylene glycol | 10.6 | 125 |
| 4. dipropylene glycol | 12.0 | 80–85 |
| 5. triol of trimethylol propane and propylene oxide, OH number 850 | 12.9 | 85–90 |
| 6. tetrol of ethylene diamine and propylene oxide, OH number 750 | 29.2 | 90–95 |

Test B: Mixed crosslinking with polyol/aromatic diamines

The stabilizing effect of the diisocyanate with respect to polyols mentioned in Example 13(A) may be further enhanced by using small quantities of an aromatic diamine.

If the amount of polyol added is changed (instead of 0.1 mole of diol, 0.09 mole of diol and 0.01 mole of the aromatic diamine DETA are used), the following thickening points are obtained:

TABLE 14

| Diol (0.09 mole) | Quantity (g) | Aromat. diamine (0.01 mole) (g) | Thickening point (°C.) |
|---|---|---|---|
| 1. ethylene glycol | 5.6 | 1.8 | 135° C. |
| 2. 1,4-butane diol | 8.1 | 1.8 | 125° C. |
| 3. diethylene glycol | 9.6 | 1.8 | 153 |
| 4. dipropylene glycol | 10.8 | 1.8 | 110 |

EXAMPLE 14

The use of stabilized naphthylene diisocyanate in a glycol-crosslinked one-component system 100 g of a polyethylene glycol adipate (OH number 56, molecular weight 2000) and 0.6 g of piperazine are mixed at 50° to 60° C., followed by the addition of 20 g of naphthylene-1,5-diisocyanate (average particle size 20±10 μm).

2.0 g of 1,4-butane diol and 0.1 g of tin-II-di(2-ethylhexanoate) are mixed into the stabilized diisocyanate suspension. The reaction mixture is stable in storage at room temperature. When heated at 120° C. for 0.8 hours, the mixture gives an elastic polyurethane molding having a shore-A-hardness of 80.

In the absence of stabilizer, heavy thickening occurs after 5 minutes at 60° C., crosslinking occurring after about 1 to 2 days at room temperature.

EXAMPLE 15

Stabilization of dimeric diphenyl methane diisocyanate and its use in one-component reactive systems

Test (A)

100 g of a polyoxypropylene diol (OH number 56, molecular weight 2000) are mixed with 0.2 g of 2,5-diamino-2,5-dimethyl hexane and 25 g of dimeric diphenyl methane-4,4′-diisocyanate, followed by the addition of 0.2 g of a 50% lead octoate solution.

Test (B)

0.2 g of the aliphatic diamine, 25 g of the dimeric isocyanate but 0.2 g of tin-II-di(2-ethylhexanoate) are similarly added to another reaction mixture of 100 g of a linear polyoxypropylene diol containing 20 mole percent of terminal oxyethylene groups (OH number 56; molecular weight 2000).

The dimeric isocyanate is prepared as follows:

0.25 g of tributyl phosphine is added with stirring to a solution of 100 g of diphenyl methane-4,4′-diisocyanate in 100 g of toluene and 100 g of petroleum ether. The dimer deposited is stirred for another 2 hours and then filtered under suction and, after washing with petroleum ether, is dried in vacuo at room temperature in the absence of moisture. The dimer is obtained substantially free from oligomers in a yield of more than 95%.

The polyurethanes obtained from both reaction mixtures (A) and (B) by heating in a mold at 110° C. for 4 hours show the properties set out in Table 15 (due to the absence of a chain-extender, the elastomer properties are at a relatively low level)

TABLE 15

|  | Tensile strength (MPa) | Breaking elongation (%) | Tear propagation resistance (KN/m) | Shore A | Elasticity (%) |
|---|---|---|---|---|---|
| Polyurethane (A) | 2.5 | 100 | 2.0 | 58 | 64 |
| Polyurethane (B) | 2.5 | 110 | 3.5 | 58 | 62 |

EXAMPLE 16

Polyurethanes based on stabilized, dimeric diphenyl methane diisocyanate are produced in varying degrees of rigidity using aromatic diamines as chain-extenders. In each case, the polyether is a linear polyoxypropylene diol containing 20% of terminal oxyethylene units (molecular weight 2000). 2,5-diamino-2,5-dimethyl hexane is used as the "amine stabilizer", DETA (2,4-/2,6-(65/35)-diamino-3,5-diethyl toluene) as the aromatic diamine and tin-II-di(2-ethylhexanoate) as the catalyst.

Formulation

TABLE 16

| | Example variants | | | |
|---|---|---|---|---|
| | 1 | 2 | 3 | 4 |
| of aliphatic diamine stabilizer | 0.3 g | 0.4 g | 0.4 g | 0.6 g |
| of dimeric diphenyl methane diisocyanate | 38.5 g | 52.0 g | 65.5 g | 79.0 g |
| of "DETA" | 5 g | 10 g | 15 g | 20 g |
| of Sn-II-octoate | 0.2 g | 0.2 g | 0.2 g | 0.2 g | per 100 g of polyether

TABLE 17

| | Mechanical properties (after heating the reactants in molds 4 h/110° C.) | | | | | |
|---|---|---|---|---|---|---|
| Test No. | Tensile strength (MPa) | Breaking elongation (%) | Tear strength (KN/m) | Shore hardness A | Shore hardness D | Elasticity (%) |
| 1 | 5.5 | 170 | 12 | 73 | 22 | 48 |
| 2 | 9.0 | 230 | 22 | 87 | 34 | 47 |
| 3 | 10.3 | 180 | 30 | 92 | 42 | 46 |
| 4 | 13.0 | 170 | 41 | 94 | 48 | 40 |

Whereas, in the absence of stabilization with the aliphatic diamine, the corresponding mixtures thicken within a few minutes to form a paste which can no longer be poured, the stabilized reactive mixtures can be stored almost indefinitely at room temperature and also remain stable in storage for several months at 50° C. Better elastomer properties are obtained with aromatic diamine chain-extenders than with polyol chain-extenders or with no chain-extenders at all.

EXAMPLE 17

Variation of the quantity of the aromatic chain-extending diamine.

General Procedure

The dimeric tolylene diisocyanate (TT) is suspended in the polyether diol. After addition of the stabilizer (3 Eq.-% of stabilizer), the mixture is stirred for 30 minutes at room temperature to stabilize the isocyanate.

After addition of the aromatic diamine chain-extender and catalyst, the mixture is heated at 120° C. After only a few minutes, it can be removed from the mold. By contrast, mixtures which have not been heated can be stored almost indefinitely at temperatures of up to 50° C.

Formulation 1 mole of polyoxypropylene ether diol, molecular weight 2000,
0.03 (1+x)mole of 2,5-diamino-2,5-dimethyl hexane
(1+x)mole of dimeric tolylene diisocyanate
x mole of 2,4-/2,6-(65/35)-diamino-3,5-diethyl toluene (DETA)
0.2 g of Pb-octoate solution per 100 parts of polyether.

Further particulars of tests 1 to 4 and the mechanical properties obtained are shown in Table 18.

TABLE 18

| | Test No. | | | |
|---|---|---|---|---|
| | 1 | 2 | 3 | 4 |
| | | | x = | |
| = parts of DETA per 100 parts of polyol | 0.56 / 5 | 1.12 / 10 | 1.68 / 15 | 2.24 / 20 |
| Mechanical properties: | | | | |
| Tensile strength [MPa] | 5.2 | 8.7 | 13.2 | 15 |
| Breaking elongation [%] | 101 | 107 | 104 | 91 |
| Tear propagation resistance [KN/m] | 6.5 | 10 | 22 | 32 |
| Shore hardness - A | 75 | 83 | 92 | 94 |
| - D | 22 | 31 | 43 | 52 |
| Elasticity [%] | 50 | 45 | 44 | 40 |
| Compression set (after 24 hr. at 70° C.) [%] | 26 | 28 | 41 | 56 |

EXAMPLE 18

Variation of the quantity of the aromatic diamine chain-extender; polyether diol containing primary OH-groups.

General Procedure

The polyol is mixed with the amine stabilizer and the diisocyanate suspended in the resulting mixture. After a reaction time of 30 minutes at room temperature, the aromatic diamine "DETA" and the catalyst are added (cf. Table 19 and the mechanical properties in Table 20). To form the polyurethane elastomers, the mixtures are heated in molds for 40 minutes at 120° C.

TABLE 19

| | Formulations: | | |
|---|---|---|---|
| Test No. | 1 | 2 | 3 |
| 1 mole of trifunctional polypropylene/polyethylene glycol block copolymer, MW 6000 (terminal oxyethylene residues containing primary OH-groups) | 100 parts | 100 parts | 100 parts |
| 0.03 to 0.1 mole of stabilizer: triamino-polypropylene ether ("T-403", a Texaco product, MW 438) | 0.11 parts | 0.2 parts | 0.4 part |
| (1.5 + x) mole of dimeric tolylene diisocyanate | with x = 3 = 26.25 parts | x = 6.72 = 48 | x = 13.5 = 89.9 |
| x mole of 2,4-/2,6-(65/35)-diamino-3,5-diethyl toluene isomer mixture (DETA) | 8.9 parts | 20 parts | 40 parts |
| Pb-II-Octoate solution (50%) | 0.2 part | 0.2 part | 0.4 part |

TABLE 20

| Mechanical properties of the polyurethanes formed | | | |
|---|---|---|---|
| Tensile strength [MPa] | 6.0 | 11.5 | 19.4 |
| Breaking elongation [%] | 225 | 200 | 20 |
| Tear propagation resistance [KN/m] | 7.7 | 26.3 | cannot be measured |
| Shore hardness - A | 81 | 94 | 99 |
| - D | 27 | 44 | 62 |
| Elasticity [%] | 55 | 44 | 42 |

EXAMPLE 19

Dependence of the hardening time upon the hardening temperature.

Test Procedure 0.4 g of ethylene diamine (1.66 Eq.-%) are dissolved as stabilizer in 400 g of polyoxypropylene ether diol, molecular weight 2000. After 140 g of dimeric tolylene diisocyanate have been stirred in, the mixture is left to react for 30 minutes to stabilize the diisocyanate. Finally, 35.6 g of the aromatic diamine "DETA" and 0.8 g of lead octoate solution are added. The mixture shows a thickening temperature of 90° C. and can be hardened within about 1 minute at 110° C. (crosslinking temperature).

Measurement Procedure

Thin layers of the mixture are applied to a Kofler heating bench and the time (in seconds) elapsing before crosslinking (hardening time) measured at various temperatures. The hardening time at temperatures of 80° C. is derived from storage tests.

TABLE 21

| Hardening temperature (°C.) | 150 | 140 | 130 | 120 | 110 | 100 | 90 | 80 | 70 | 60 | 50 |
|---|---|---|---|---|---|---|---|---|---|---|---|
| Hardening time (seconds) | 10 | 15 | 25 | 40 | 70 | 150 | 360 | $10^3$ | $5 \times 10^3$ | $10^5$ | (extrapolated values from storage tests) |

EXAMPLE 20

Dependence of the hardening temperature upon the quantity of amine stabilizer.

Test Procedure

Same formulation as in Example 19 with different quantities of ethylene diamine.

Measurement Procedure

The hardening temperature required for a hardening time of 1 minute and also the thickening temperature are determined on a Kofler heating bench for different additions of amine stabilizer. Some thickening temperatures are more accurately determined using a test tube in an oil bath and show satisfactory consistency with the temperatures determined on the Kofler bench.

TABLE 22

| Mole % of ethylene diamine, based on TT | 0.25 | 0.5 | 1.0 | 1.66 | 3.33 |
|---|---|---|---|---|---|
| Thickening temp. (°C.) | RT | RT | 65 | 90 | 110 |
| Hardening temp. (°C.) | 88 | 92 | 100 | 110 | 120 |

EXAMPLE 21

Combined effect of two different amine stabilizers.

Formulation 100 g (0.05 mole) of polyoxypropylene ether diol, MW=2000,
x g of aliphatic diamine stabilizer,
35 g of dimerized tolylene-2,4-diisocyanate (TT)
8.9 g of 2,4-/2,6-diamino-3,5-diethyl toluene isomer mixture (DETA)
0.2 g of Pb-octoate solution (50% in cleaning spirit).

Test Procedure (a) 0.1 g of ethylene diamine is dissolved in the polyol. After the addition of TT, the mixture is stirred for 30 minutes at room temperature, after which the chain extender and the catalyst are added.

(b) 0.2 g of 2,5-diamino-2,5-dimethyl hexane are dissolved in the polyol. The further procedure is then the same as in (a).

(c) 0.05 g of ethylene diamine are dissolved in the polyol. The total quantity of TT is allowed to react for 15 minutes with the polyol/ethylene diamine mixture. After the addition of 0.1 g of 2,5-diamino-2,5-dimethyl hexane, the reaction mixture is stirred for another 15 minutes at room temperature. The further procedure is then the same as in (a).

(d) The procedure is the same as in (c) using first 0.1 g of 2,5-diamino-2,5-dimethyl hexane and then 0.05 g of ethylene diamine for stabilization.

The thickening temperature is then determined in the same way as in Example 2.

The surface quality of a molding produced by heating at 120° C. in an open casting mold was assessed.

TABLE 23

| Test | (a) | (b) | (c) | (d) |
|---|---|---|---|---|
| Surface quality | slightly uneven | smooth | smooth | smooth |
| Thickening temperature | 90° C. | 60° C. | 80° C. | 70° C. |

This Example shows that it is possible further to optimize the processing properties of one-component systems by applying two different protective layers one above the other to the same diisocyanate grain. In test (c), the inner layer based on ethylene diamine produces a higher thickening temperature by comparison with test (b), while the other protective layer based on 2,5-diamino-2,5-dimethyl hexane provides for a good heating temperature and for high quality of the heated polyurethanes.

EXAMPLE 22

The use of stabilized polyisocyanates for the production of foamed polyurethanes.

To produce a foamed molding, the following polyol components are first intensively mixed with one another for 30 seconds at room temperature using a high-speed stirrer:

| | |
|---|---|
| 70 parts of polyol A (polyether, functionality 2, MW 4000, adduct of propylene oxide (80 parts by weight) and ethylene oxide (20 parts by weight) with propylene glycol) | |
| 20 parts of polyol B (polyether, functionality 3, MW 4800, adduct of propylene oxide and ethylene oxide (50/50) with 1,1,1-trimethylol propane) | |
| 1 part of ethylene glycol | |
| +14 parts of 1,4-butane diol | |
| 105 parts of polyol mixture | |

39 parts of dimerized 2,4-tolylene diisocyanate are then uniformly dispersed in the polyol mixture under the same conditions and the solid polyisocyanate is coated by the addition immediately afterwards of 0.72 part of 2,5-diamino-2,5-dimethyl hexane. After about 15 minutes, 0.72 part of a silicone/polyether copolymer (foam stabilizer OS-50, a product of Bayer AG), 0.28 part of an approximately 50% solution of lead-II-octoate (as catalyst) and 8.7 parts of trichlorofluoromethane (as blowing agent) are mixed in. The mixture is introduced in 2 seconds into a vertically arranged mold thermostatically controlled to a temperature of 80° C. After 10 minutes, a 10 mm thick highly elastic test plate having a gross density of 786 kg/m$^3$ is removed from the mold. The test plate has a surface hardness of 50 Shore-A. In the absence of the blowing agent, the mixture used for producing the foamed test plate remains stable in storage for several months at room temperature. However, if the aliphatic diamine is not added, the mixture solidifies with about 24 hours and can no longer be processed.

EXAMPLE 23

Reaction of one-component reactive polyurethane mixtures by trimerization (addition of catalyst) to form the polyurethane.

A mixture of 100 parts of a polyoxypropylene amine, molecular weight 2000 (Jeffamine D 2000, a product of the Texaco Chem. Company, USA) and 0.75 part of ethylene diamine is intensively mixed at room temperature with 62.5 parts of finely powdered 4,4'-diisocyanatodiphenyl methane (NCO:amine-equivalent ratio=5:1). A storable mixture which hardens in 30 seconds at 90° C. is obtained after the addition of 2 g of N,N',N"-tris(3-dimethylaminopropyl)-s-triazine. If, instead of thermal hardening, 10 g of dimethyl formamide are added to the mixture at room temperature, the reactive mixture hardens very rapidly with evolution of heat.

The highly elastic, rigid test specimens obtained are insoluble in boiling dimethyl formamide. They show the IR absorption bands typical of the isocyanurate ring.

EXAMPLE 24

Variation of the thickening point and stability in storage by the addition of solvents. Production of the starting material 2000 g of a linear polyether (OH number 56, molecular weight 2000, 80% by weight of propylene oxide and 20% by weight of ethylene oxide units) are intensively mixed with 1 g of ethylene diamine. 700 g of dimerized 2,4-tolylene diisocyanate are introduced into the resulting mixture, followed by intensive stirring. About 20 minutes after the end of stirring, 180 g of diethyl tolylene diamine-DETA-(35% of 2,6-diamino- and 65% of 2,4-diamino-3,5-diethyl toluene) and 4 g of an approximately 50% solution of lead di(2-ethylhexoate) in aliphatic hydrocarbons (petrol ether, boiling range 50°–80° C.) are mixed in.

A measured quantity by volume of a solvent is added to 50 g of the above mixture, the thickening point determined (for procedure, see Example 2) and the behavior of the test specimen in storage is observed. The results are set out in Table 24 below.

EXAMPLE 25

Crosslinking by shear forces which break up the layer of coating.

A one-component mixture liquid at room temperature and stable in storage (stability in storage $\geq 3$ months at room temperature) prepared by mixing at room temperature 0.05 mole of a linear polyoxypropylene ether diol containing 20% of terminal ethylene oxide units, molecular weight 2000, 0.05 g of 2,5-diamino-2,5-dimethyl hexane, 0.1 mole of dimeric tolylene diisocyanate and 0.05 mole of the aromatic diamine "DETA" and 0.2 g of a 50% lead octoate solution is exposed to severe mechanical stressing in a high-speed mixer (a Braun Starmix) with the crossed blades rotating at approximately 5000 r.p.m. The temperature of the reaction mixture rises to 35°–40° C. during the 2 to 3 minute stirring process. Thereafter the still liquid mixture is poured into a cold mold. After a short time, the mixture begins to solidify and, after 10 to 20 hours at room temperature, an elastic molding having a hardness of from 75 to 80 (shore A) is obtained. The crosslinking

TABLE 24

| Solvent | Quantity per 50 g of mixture | Thickening point | Storage behavior at room temperature |
|---|---|---|---|
| None | — | 80° C. | stable in storage for 4 weeks |
| Dimethyl formamide | 1.0 ml | 75° C. | solidification after about 10 days |
| | 2.5 ml | 75° C. | solidification after about 6 days |
| | 5.0 ml | 67° C. | solidification after about 30 mins |
| | 12.5 ml | | solidification after about 15 mins |
| Tetramethylene sulfone | 1.0 ml | 80° C. | solidification after about 12 days |
| | 2.5 ml | 75° C. | solidification after about 12 days |
| | 5.0 ml | 70° C. | solidification after about 12 days |
| | 12.5 ml | 65° C. | solidification after about 12 days |
| Propylene carbonate | 1.0 ml | 68° C. | solidification after about 12 days |
| | 2.5 ml | 65° C. | solidification after about 9 days |
| | 5.0 ml | 65° C. | solidification after about 9 days |
| | 12.5 ml | 65° C. | solidification after about 6 days |
| | 20 ml | 60° C. | solidification after about 6 days |
| Dimethyl acetamide | 1.0 ml | 75° C. | solidification after about 12 days |
| | 2.5 ml | 65° C. | solidification after about 6 days |
| | 5.0 ml | — | solidification after about 30 mins |
| | 12.5 ml | — | solidification after about 15 mins |
| N—methyl pyrrolidone | 1.0 ml | 76° C. | solidification after about 12 days |
| | 2.5 ml | 70° C. | solidification after about 10 days |
| | 5.0 ml | — | solidification after about 30 mins |
| | 12.5 ml | — | solidification after about 15 mins |
| Nitrobenzene | 1.0 ml | 80° C. | solidification after about 12 days |
| | 2.5 ml | 76° C. | solidification after about 12 days |
| | 5.0 ml | 67° C. | solidification after about 10 days |
| | 12.5 ml | — | solidification after about 30 mins |
| Benzonitrile | 1.0 ml | 78° C. | solidification after about 12 days |
| | 2.5 ml | 75° C. | solidification after about 12 days |
| | 5.0 ml | 70° C. | solidification after about 10 days |
| | 12.5 ml | — | solidification after about 30 mins. |
| N,N'—tetramethyl urea | 1.0 ml | 75° C. | solidification after about 12 days |
| | 2.5 ml | 70° C. | solidification after about 12 days |
| | 5.0 ml | 67° C. | solidification after about 10 days |
| | 12.5 ml | — | solidification after about 15 mins |
| o-dichlorobenzene | 1.0 ml | 80° C. | solidification after about 12 days |
| | 2.5 ml | 70° C. | solidification after about 10 days |
| | 5.0 ml | 70° C. | solidification after about 10 days |
| | 12.5 ml | 62° C. | solidification after about 6 days |
| Chlorobenzene | 1.0 ml | 80° C. | solidification after about 12 days |
| | 2.5 ml | 80° C. | solidification after about 12 days |
| | 5.0 ml | 70° C. | solidification after about 20 days |
| | 12.5 ml | 65° C. | solidification after about 6 days |
| Toluene | 1.0 ml | 75° C. | solidification after about 12 days |
| | 2.5 ml | 67° C. | solidification after about 12 days |
| | 5.0 ml | 65° C. | solidification after about 12 days |
| | 12.5 ml | 60° C. | solidification after about 6 days |
| Cleaning spirit | 1.0 ml | 80° C. | solidification after about 12 days |
| | 2.5 ml | 78° C. | solidification after about 12 days |
| | 5.0 ml | 72° C. | solidification after about 12 days |
| | 12.5 ml | 70° C. | solidification after about 8 days | time can be considerably reduced (5 to 10 hours at room temperature) by the addition of small quantities of polar solvents (for example 3 to 5% of N-methyl pyrrolidone, based on 100 g of mixture).

EXAMPLE 26

One-component mixture based on an aromatic aminopolyether.

Formulation 100 g of an aromatic aminopolyether based on a polyoxypropylene ether diol (molecular weight 2000)/tolylene diisocyanate (molar ratio 1:2) produced in accordance with German Offenlegungsschrift No. 29 48 419; amine number 46.7; MW 2350, 0.35 q of piperazine, 12 g of ground 1,5-diisocyanatonaphthalene (particle size 1–20 μm).

Test Procedure

The piperazine is dissolved in the aminopolyether and the finely ground diisocyanate rapidly introduced into the resulting solution. A suspension of the stabilized diisocyanate which is highly stable in storage at room temperature is obtained.

After the mixture has been heated at 120° C. (for 30 to 60 minutes), elastic moldings having the following mechanical properties are obtained:

TABLE 25

| Shore hardness - A | 90 |
| - D | 30 |
| Tensile strength [MPa] | 9.5 |
| Breaking elongation [%] | 200 |
| Tear propagation resistance [KN/m] | 15.5 |
| Elasticity [%] | |

EXAMPLE 27

A solution of 8.9 g (0.05 mole) of 2,4-diamino-3,5-diethyl toluene and 0.2 g of lead octoate (Octa-Soligen Lead) is added to a suspension of 34.8 g (0.1 mole) of TT in 100 g (0.05 mole) of a linear PPG-ether (molecular weight: 2000, OH number 56). The reaction mixture has a pouring time of approximately 5 minutes at room temperature and solidifies after 10 to 15 minutes to form a stiff paste-like mass (comparison test). If, by contrast, the quantities of 2,5-diamino-2,5-dimethyl hexane indicated in the following Table are added to the above suspension before the aromatic diamine and lead compound, the solidification times of the mixtures are distinctly lengthened.

TABLE 26

| | Aliphatic diamine (g) (stabilizer) | Solidification time at RT |
|---|---|---|
| 1. | — (comparison) | 10–15 minutes |
| 2. | 0.005 g (0.035 mole %) | 30 minutes |
| 3. | 0.01 (0.07 mole %) | 1.0 hour |
| 4. | 0.015 (0.104 mole %) | 1.5 hours |
| 5. | 0.02 (0.15 mole %) | 2.0 hours |

EXAMPLE 28

A solution of 6.2 g (0.1 mole) of ethylene glycol and 0.3 g of a lead octoate solution (Octa-Soligen PB-24, a product of the Borchers Company, Dusseldorf) is added to a suspension of 52.2 g (0.15 mole) of dimerized tolylene 2,4-diisocyanate in 100 g (0.05 mole) of a linear polypropylene glycol ether (molecular weight: 2000, OH number: 56). The suspension formed has a viscosity of approximately 2000 cP (25° C.). The reaction mixture has a pouring time at room temperature of approximately 1 hour and solidifies after about 3 hours to form a stiff paste-like mass. If, by contrast, the quantities of 2,5-diamino-2,5-dimethyl hexane indicated in the following Table are added to the above suspension before the ethylene glycol and the lead compound, the solidification time of the mixtures is distinctly lengthened:

TABLE 27

| | g of aliphatic diamine (mole %, based on diisocyanate) | Solidification time |
|---|---|---|
| 1. | — | approx. 3 hours |
| 2. | 0.011 g 0.05% | approx. 6 hours |
| 3. | 0.054 g 0.25% | approx. 12 hours |
| 4. | 0.108 g 0.5% | approx. 24 hours |
| 5. | 0.216 g 1.0% | after 5 days: visc. 23,000 cP (still pourable) |
| 6. | 0.432 g 2.0% | after 5 days: visc. 17,000 cP (still pourable) |

EXAMPLE 29

(a) A mixture of a stabilized diisocyanate in a relatively high molecular weight polyamine.

0.4 part of 4,4'-diamino-3,3'-dimethyl dicyclohexyl methane are dissolved as amine stabilizer in 100 parts of an aromatic, relatively high molecular weight polyether polyamine having an NH-number of 80.4 (produced as described in (c) below). 54.2 parts of finely ground dimeric tolylene-2,4-diisocyanate are suspended at 60° C. in the resulting mixture. After stirring for 30 minutes at 60° C., 20 parts of molten 3,5,3',5'-tetraethyl-4,4'-diamino diphenyl methane are slowly stirred in. After stirring for another 4 hours at 70° C., a casting composition completely stable in storage at 70° C. is obtained having a thickening temperature of 100° C. and a viscosity of 18 Pa.s at 50° C. or 1.5 Pa.s at 76° C.

(b) The use of (a) for the production of polyurethane

To produce a rigid elastomer plate, the casting composition is introduced into an open casting mold coated with a silicone release agent and solidified and tempered for 6 hours at 120° C. An elastomer having the mechanical properties shown in Table 28 is obtained:

TABLE 28

| Example No. | 29 | 30 | 31 | 32 | 33 |
|---|---|---|---|---|---|
| Tensile strength [MPa] (DIN 53 504) | 19 | 3.5 | 4.0 | 9.5 | 15 |
| Breaking elongation [%] (DIN 53 504) | 80 | 150 | 150 | 200 | 420 |
| Tear propagation [KN/m] resistance (DIN 53 515) | 94 | 5.0 | 4.5 | 12.1 | 42 |
| Shore hardness (DIN 53 505) - A | 100 | 72 | 70 | 87 | 90 |
| - D | 70 | 21 | 20 | 35 | — |
| Elasticity [%] (DIN 53 512) | 47 | 61 | 62 | 40 | 57 |

(c) Production of the relatively high molecular weight polyamine.

1 mole of a linear polypropylene glycol having an OH number of 112 (molecular weight 1000) and 2 moles of tolylene-2,4-diisocyanate are converted into an NCO-prepolymer by heating for 4 hours at 80° C. A 5% solution of the NCO-prepolymer in acetone is then added to a 10% aqueous sodium hydroxide solution (2.2 moles of NaOH) at such a rate that the reaction temperature does not exceed 25° C. The reaction mixture is then stirred for another 30 minutes at that temperature, followed by refluxing for 2 hours. After standing for 30 minutes, the lower aqueous salt solution is separated off from the two-phase reaction mixture and discarded. The upper phase is freed from residues of water and acetone at 20 mbar/80° C. and then at 1 mbar/100° C. Small residues of salt are separated off and the polyether amine, which has an NH number of 80.4 (molecular weight 1390), is isolated by filtering the product (temperature 60° C.) through a pressure filter (3 bars excess pressure).

EXAMPLE 30

(a) Preparation of the polyisocyanate suspension 9.7 parts of dimeric tolylene-2,4-diisocyanate are suspended at room temperature in 100 parts of a difunctional, relatively high molecular weight aliphatic polyether diamine having an NH number of 28 (produced as described in (c) below). A casting composition, where less than 25 equivalent percent of the isocyanate groups have reacted with the amino groups, which is completely storable at 50° C. is obtained, having a viscosity at room temperature of 0.8 Pa.s and a thickening temperature of 80° C.

(b) Use for the production of an elastomer plate

The casting composition is introduced into an open mold coated with a silicone release agent and then solidified and tempered for 6 hours at 120° C. By further reaction at the high temperature, an elastomer having the properties indicated in Table 28 is obtained.

(c) Production of the relatively high molecular weight aminopolyol

The relatively high molecular weight, difunctional aliphatic polyether diamine (NH number 28) is obtained from a linear polypropylene ether diol (OH number 28) by reductive amination with ammonia/hydrogen in accordance with Belgian Patent 634,731.

EXAMPLE 31

(a) Preparation of the polyisocyanate suspension 0.1 part of 4,4'-diamino-3,3'-dimethyl dicyclohexyl methane is dissolved in 100 parts of an aliphatic, relatively high molecular weight polyether triamine having an NH number of 37.8 (produced as described in Example 42(c)) and 12.12 parts of dimeric, finely powdered tolylene-2,4-diisocyanate are suspended in the resulting solution at 35° C. A casting composition which is completely stable in storage at 50° C. is obtained, having a viscosity at room temperature of 1 Pa.s and a thickening temperature of 70° C. The reaction of the NCO-groups and the amine groups of the polyether triamine comes to a halt after less than 25 equivalent percent of the isocyanate groups have reacted.

(b) Use for the production of polyurethanes

To produce an elastomer plate, the casting composition is introduced into an open casting mold coated with a silicone release agent and then solidified and tempered for 6 hours at 120° C. whereby the reaction of isocyanate and amine groups proceeds to form the final product. An elastomer plate having the properties set out in Table 28 is obtained.

EXAMPLE 32

(a) Preparation of the polyisocyanate suspension 0.2 part of 4,4'-diamino-3,3'-dimethyl dicyclohexyl methane is dissolved in 100 parts of an aliphatic, relatively high molecular weight polyether triamine having an NH number of 35 (produced as described in (c) below). 29.5 parts of dimeric tolylene-2,4-diisocyanate are suspended at 20° C. in the resulting solution. After stirring for 30 minutes at room temperature, 8.9 parts of an isomer mixture of 2,4-diamino- and 2,6-diamino-3,5-diethyltoluene (isomer ratio 65:35) are added as chain-extending agent. A casting composition, where the isocyanate is stabilized by reaction of less than 25 equivalent percent of the isocyanate groups, which is completely stable in storage at up to 50° C. is obtained, having a viscosity at room temperature of 1.3 Pa.s and a thickening temperature of 80° C.

(b) Use of the suspension for the production of polyurethanes

To produce an elastomer plate, the casting composition is introduced into an open casting mold coated with a silicone release agent and then solidified and tempered for 6 hours at 120° C., whereby the isocyanate/amine reaction is completed. An elastomer having the properties set out in Table 28 is obtained.

EXAMPLE 33

(a) Preparation of the polyisocyanate suspension 200 parts of the relatively high molecular weight aromatic polyether diamine produced as described in (c) below (NH number 47.4) are mixed with 0.5 part of ethylene diamine and 0.2 part of 3,3'-dimethyl-4,4'-diaminodicyclohexylmethane. 20 parts of powdered 1,5-diisocyanatonaphthalene are then added. This mixture remains stable in storage for at least 2 months at room temperature. At 120° C., however, it solidifies rapidly.

(b) Use of the suspension for the production of polyurethanes

After solidification at 120° to 125° C., reaction mixtures poured into casting molds spray-coated with silicone release agent give highly elastic polyurethane elastomers having the properties shown in Table 28.

(c) Production of the relatively high molecular weight polyamine 1 mole of a linear polypropylene ether glycol (OH number 56) and 2 moles of tolylene-2,4-diisocyanate are converted into an NCO-prepolymer (NCO-content 3.58%) by heating for 4 hours at 80° C. 810 g of the NCO-prepolymer (temperature 45° C.) are then added with intensive stirring to a cooled solution of 52.2 g of potassium hydroxide and 500 ml of water and 300 ml of acetone (NCO:OH⊖-ratio=1:1.35) at such a rate that an internal temperature of 25° C. is not exceeded. The reaction mixture is then stirred for another 30 minutes at that temperature, followed by refluxing for 2 hours. After standing for 30 minutes, the lower aqueous salt solution is separated off from the two-phase reaction mixture and discarded. The upper phase is freed from residues of water and acetone at 20 mbar/80° C. and then at 1 mbar/100° C. Small residues of salt are separated off and the polyether amine, which has an NH number of 47.4, is isolated by filtering the product (50° C.) through a pressure filter (3 bars excess pressure).

EXAMPLE 34

(a) Preparation of the polyisocyanate suspension 30 parts of bis-(3,3'-diisocyanato-4,4'-dimethyl phenyl)-urea, 30 parts of a linear polypropylene ether diol (molecular weight 2000) and 100 parts of the aromatic polyether diamine produced in accordance with Example 33(c) (NH number 47.4) are suspended at room temperature using a Starmix. A solution of 0.6 part of 3,3'-dimethyl-4,4'-diaminodicyclohexyl methane in 100 parts of the aromatic polyether diamine mentioned in Example 33(c) (NH number 47.4) is then stirred in. The suspension of the stabilized diisocyanates is stable in storage at room temperature.

(b) Use of the suspension for the production of elastomers

The suspension hardens quickly at 120° C. After curing for 2 to 4 hours at 120° C., highly elastic moldings having a shore A hardness of from 85 to 87 are obtained.

EXAMPLE 35

(a) Preparation of the polyisocyanate suspension 0.15 part of 3,3'-dimethyl-4,4'-diaminodicyclohexylmethane and 16.8 parts of dimeric tolylene-2,4-diisocyanate are dispersed in 100 parts of the aromatic polyether polyamine produced in accordance with Example 33(c) (NH number 47.4).

(b) Use of the stabilized polyisocyanate suspension

The storable one-component system produced in accordance with (a) is processed by the methods described below, the moldings obtained differing in shape according to the geometry of the mold.

1. Dip Process

An elongate, thin-walled cylindrical glass flask 3 cm in diameter filled with silicone oil heated to 120° C. was dipped into the one-component system heated to 50° C. The outer surface of the glass cylinder was coated with silicone release agent. The one-component system solidifies spontaneously on the heated wall of the cylinder, a time of about 1 minute being required for a layer thickness of 1 mm. The liquid system solidifies only on the hot glass wall. Thin-walled to thick-walled, highly elastic hollow bodies characterized by favorable mechanical properties are obtained according to the dipping time.

2. Rotation Process

The above one-component system was heated to 50° C. and the now readily pourable reaction mixture is poured carefully into a iron tube 4 cm in diameter (in smaller quantities than corresponds to the volume of the tube). Both ends of the tube are then closed. During the following rotation of the tube horizontally of its longitudinal axis, the tube wall is uniformly heated from outside to 110°–130° C. by means of a hot air fan. After brief rotation, the tube is left with an internal coating which varies in thickness depending upon the amount of one-component system introduced into the tube.

3. Slush Molding

A mold heated to 50°–80° C. is filled with the one-component system, followed by heating to 120° C. Solidification of the system initially takes place on the inner wall of the mold and then gradually progresses inwards. Due to the relatively poor thermal conductivity of the solidified outer layers, the core of the mold remains liquid for a relatively long time. After a certain time (by the end of which the mold core has still not solidified), the mold is emptied and the molding is removed and tempered for 4 to 5 hours at 120° C.

As in the dip process, the wall thickness of the elastomer depends upon the heating time. Since the still liquid material is still entirely useable, this work cycle may be repeated indefinitely after addition of the missing quantity.

EXAMPLE 36

(a) Preparation of the stabilized polyisocyanate suspension 0.07 part of 2,5-diamino-2,5-dimethyl hexane is added as amine stabilizer to a mixture of 100 parts of a long-chain aromatic polyether polyamine having an NH number of 47 (produced as in Example 33(c), 1.15 parts of diazabicyclooctane (as catalyst) and 0.6 part of an ethylene oxide/propylene oxide/dimethyl siloxane block polymer as surface-active silicone. 16.54 parts of dimerized 2,4-tolylene diisocyanate are then stirred in over a period of 1 minute using a high-speed stirrer. A storable suspension is obtained.

(b) Use of the suspension for the production of polyurethanes 800 parts of the suspension thus obtained are intensively mixed with 200 parts of copper powder, followed by degassing (water jet vacuum, room temperature, 1 hour). 1000 g of this mixture are then introduced over a period of about 3 seconds from below into a vertical plate mold heated to 95° C. (molding dimensions $20\times39.4\times1$ cm). After 5 minutes, an elastic molding is obtained, having a surface hardness of 94 Shore A (43 Shore D/25° C.) and a density of 1.27 g/cc. The surface of the molding is faultless.

EXAMPLE 37

(a) Preparation of the suspension of the stabilized diisocyanate 0.07 part of 2,5-diamino-2,5-dimethyl hexane is added to a mixture of 100 parts of a long-chain, aromatic polyether diamine having an NH number of 47.4 (produced as in Example 33c), 1.15 parts of diazabicyclooctane (as catalyst) and 0.6 part of a polyether siloxane block copolymer (Bayer-Silicone-OS-50,BAYER AG, D-5090 Leverkusen).16.54 parts of dimerized 2,4-tolylene diisocyanate are then stirred in using a high-speed stirrer. A storable suspension is obtained. A vigorous stream of air is then passed through for about 2.5 hours to obtain a creamy suspension.

(b) Use of the suspension

Without any more stirring, 590 g of the creamy suspension are introduced over a period of about 2 seconds from below into a vertical plate mold heated to 95° C. (molding dimensions $20\times39.4\times1$ cm). A molding having a surface hardness of 73 Shore A (at 25° C.), a density of 0.75 g/cc and an integral density distribution (solid surface skin, cellular core) is removed from the mold after 5 minutes. The surface of the molding is faultless.

EXAMPLE 38 (Comparison Example)

88.5 parts of dimerized 2,4-tolylene diisocyanate are stirred over a period of 2 minutes into a mixture of 40 parts of a polyether (OH 42, average functionality 2.78, molecular weight 3700 and obtained by the addition of ethylene oxide and propylene oxide to a mixture of trimethylol propane and propylene glycol), 60 parts of a trifunctional polyol (OH number 865) obtained by the addition of 0.9 mole of propylene oxide onto 1 mole of trimethylol propane, 0.2 part of an approximately 50% solution of lead-II-octoate in petrol and x parts of 3,3'- dimethyl-4,4'-diaminodicyclohexyl methane (as amine stabilizer). The viscosity of the samples prepared is observed for several days.

TABLE 29

Table 29 shows the viscosities in mPa.s at 25° C. as a function of x and the storage time in days.

| [Days] Time | $x_O$ (Comparison) | 0.5 |
|---|---|---|
| 0 | 26,000 | 40,000 |
| 1 | 200,000 | 65,000 |
| 2 | >400,000 | 65,000 |
| 5 | solid | 65,000 |
| 8 | solid | 70,000 |
| 14 | solid | 70,000 |

As the Comparison Test shows, the dimeric tolylene-2,4-diisocyanate—by storage in OH-polyethers plus low molecular weight polyols—continues to react at its surface until the system solidifies, it does not form a "stabilizing coating" which retards the reactivity of the polyisocyanate.

It is only a polyurea-coated polyisocyanate of reduced reactivity which produces a reaction with a small quantity of an aliphatic diamine, leading to stable one-component reactive polyurethane mixtures.

EXAMPLE 39

The following are dissolved in quantities of 1000 g of a linear polypropylene ether diol (molecular weight 2000):

Test 1 1.66 g of hydrazine hydrate
Test 2 3.0 g of methyl hydrazine
Test 3 2.0 g of hydrazinoethanol.

Quantities of 35 g of dimeric tolylene diisocyanate in the form of a fine powder are then stirred in. After stirring for 30 minutes at room temperature, quantities of 89 g of a 2,4-/2,6-diamino-3,5-diethyl toluene (65/35) isomer mixture and 2.0 g of lead octoate solution are added to the suspension of the stabilized polyisocyanate.

The mixtures are stable in storage and have the thickening temperatures indicated in Table 30.

To produce elastomer test plates, the casting composition is introduced into an open casting mold coated with silicone release agent and then solidified and tempered for 6 hours at 120° C. The elastomers obtained have the properties shown in Table 31.

TABLE 30

| Test No. (Example 2) | Type of "amine stabilizer" | Quantity of stabilizer in g | in Equiv.-% | Thickening temperature in °C. |
|---|---|---|---|---|
| 1 | hydrazine hydrate | 3.32 | 3.33 | 60 |
| 2 | methyl hydrazine | 6.0 | 12.0 | 90 |
| 3 | hydrazinoethanol | 4.0 | 6.0 | 85 |
| 4 | none (Comparison Test) | instantaneous thickening after addition of the DETA and complete crosslinking over a period of one week at room temperature* | | |

*In this case, "thickening" at a temperature as low as room temperature is indicative of an inadequate "stabilizing effect" (coating reaction) of the "stabilizer".

TABLE 31

| Mechanical properties of heated polyurethanes | | | |
|---|---|---|---|
| Example 3/Test No. | 1 | 2 | 3 |
| Tensile strength*** (DIN 53 504) [MPa] | 8.9 | 8.7 | 8.3 |
| Breaking elongation (DIN 53 504) [%] | 150 | 160 | 165 |

TABLE 31-continued

| Mechanical properties of heated polyurethanes | | | |
|---|---|---|---|
| Example 3/Test No. | 1 | 2 | 3 |
| Tear propagation*** resistance (DIN 53 515) [KN/m] | 11.0 | 10.6 | 11.1 |
| Shore hardness*** (DIN 53 505) -A | 91 | 88 | 87 |
| -D | 34 | — | — |
| Elasticity*** (DIN 53 512) [%] | 46 | 47 | 44 |

***In the following Examples, the values are also determined in accordance with the DIN-standards quoted.

EXAMPLE 40

40.0 g of a solution of oxalic acid hydrazide methyl hydrazide

(10% in ethylene glycol) are dispersed in 1000 g of a relatively high molecular weight aromatic polyether diamine having an NH number of 80.4 (produced as described in Example 29(c)). 475 g of finely powdered dimeric tolylene-2,4-diisocyanate are suspended in this hydrazide solution in the aminopolyether. A casting composition which is completely stable at room temperature (storage time tested for 3 months at room temperature) is obtained. This casting composition has a viscosity at 50° C./18 Pa.s and a shelf life at 50° C. of several days.

Above 60° C., the casting composition thickens through polymerization, i.e., when 10 to 20 g of the casting composition are slowly heated, rapid thickening occurs above 60° C.

To produce an elastomer plate, the casting composition is introduced into an open casting mold coated with silicone release agent and solidified and tempered for 6 hours at 120° C. An elastomer having the properties shown in Table 32 is obtained.

TABLE 32

| Mechanical properties of heated polyurethanes | | | |
|---|---|---|---|
| Example No. | 40 | 41 | 42 |
| Tensile strength [MPa] (DIN 53 504) | 22 | 25 | 16 |
| Breaking elongation (DIN 53 504) [%] | 100 | 400 | 800 |
| Tear propagation resistance (DIN 53 515) [KN/m] | 50 | 55 | 46 |
| Shore Hardness (DIN 53 505) - A | 99 | 94 | 89 |
| - D | 64 | 39 | 33 |
| Elasticity (DIN 53 512) [%] | 38 | 52 | 60 |

EXAMPLE 41

3.0 g of a 20% solution of β-semicarbazidopropionic acid hydrazide $H_2N.HN.CO.NH.CH_2.CH_2.CO.NH.NH_2$ in hot diethylene glycol are stirred into 1000 g of a relatively high molecular weight aromatic polyether diamine having an NH number of 47.4 (produced as described in Example 33(c)) and 166 g of dimeric tolylene-2,4-diisocyanate are suspended in the resulting mixture. A casting composition which is completely stable in storage at 50° C. is obtained, its viscosity amounting to 3 Pa.s at 50° C. The casting composition thickens up very quickly at temperatures above 78° C.

The casting composition is thermally solidified to form an elastomer test plate in the same way as described in Example 40, the test plate having the properties shown in Table 32.

EXAMPLE 42

(a) Suspension of a hydrazide-stabilized polyisocyanate in a relatively high molecular weight polyamine 8.0 g of a 50% solution of ethylene-bis-semicarbazide

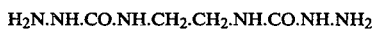

in hot water are stirred into 1000 g of a relatively high molecular weight polyether polyamine containing aromatic terminal groups and having an NH number of 37.8 (produced as described below) and the resulting mixture freed from water at 100° C./0.3 mbar. 130 g of dimeric tolylene-2,4-diisocyanate are suspended in the resulting solution of the bis-semicarbazide in the aminopolyether. A casting composition which is completely stable in storage at up to 50° C. is obtained, its viscosity amounting to 1.3 Pa.s at 50° C. The casting composition has a thickening temperature of 90° C.

(b) Use

To produce an elastomer test plate, the casting composition is solidified and tempered for 6 hours at 120° C. in molds in the same way as in Example 40. The properties of the elastomer are shown in Table 32.

(c) The relatively high molecular weight polyether polyamine is produced as follows:

1 mole of a linear polypropylene glycol (OH number 42.6) and 2 moles of tolylene-2,4-diisocyanate are converted into an NCO-prepolymer (NCO-content 2.82%) by heating for 4 hours to 80° C. 1000 g of the NCO-prepolymer (temperature 45° C.) are then added with intensive stirring to a cooled solution of 52.2 g of potassium hydroxide and 500 ml of water and 400 ml of acetone (NCO:OH$^\ominus$-ratio-1:1.35) at such a rate that an internal temperature of 25° C. is not exceeded. The reaction mixture is then stirred for another 30 minutes at that temperature, followed by refluxing for 2 hours. Working up is carried out in the same way as in Example 29(a). The aminopolyether has an NH-number of 37.8.

EXAMPLE 43

(a) Preparation of a storable coating paste

A solution heated to 50° C. of 0.6 g of β-semicarbazido-propionic acid hydrazide in 2.4 g of diethylene glycol is stirred together with 10 g of a 2,4-/2,6-diamino-3,5-diethyltoluene isomer mixture (65/35)-DETA-into 1000 g of a linear aromatic aminopolyether having an NH number of 47.4 (produced as described in Example 33(c)), followed by the addition of 186 g of finely powdered 4,4'-diisocyanato-3,3'-dimethyl diphenyl uret dione (dimeric tolylene diisocyanate). The resulting reactive mixture with the suspended polyadduct-coated diisocyanate is stable in storage at room temperature despite the presence of the dissolved aromatic diamine chain-extender agent. 10% by weight of a pigment preparation of 50 parts of titanium dioxide in 50 parts of dioctyl phthalate are added to the reaction mixture for pigmenting purposes. The spreadable paste has a viscosity of 20,000 mPa.s at 25° C.

(b) Use for coating textiles

A polyester fabric (220 g/m²) is coated on both sides by direct spread coating in a coating machine. Using a coating knife, the coating composition is applied to the first side of the fabric in a quantity of 250 g/m² and reacted in a 12 meters long drying tunnel at tunnel temperatures of 120/130/130° C. for a rate of travel of 6 meters per minute. The fabric is then coated (180 g/m²) on the other side and heated in exactly the same way. The coating obtained is free from bubbles on both sides and shows outstanding adhesion to the non-primed polyester fabric.

If a film is similarly produced from the spreading paste by knife coating onto a separating paper, the 100% modulus value of the film amounts to 10–11% Mpa.

EXAMPLE 44

(a) Preparation of a storable coating paste 750 g of a linear aromatic aminopolyether having an NH number of 47.4 (produced as described in Example 33(c)) and 250 g of an aliphatic aminopolyoxypropylene ether having an NH number of 35 (produced by the reductive amination of a trimethylolpropane-branched polyoxypropylene glycol) are mixed with 1.3 g of 3,3'-dimethyl-4,4'-diaminodicyclohexylmethane. 150 g of finely divided, dimeric tolylene-2,4-diisocyanate are then introduced with stirring, resulting in the formation of a polyurea-coated diisocyanate suspension in polyaminoethers (viscosity 10,000 mPa.s/25° C., shelf life at least 3 months).

(b) Use for the solvent-free coating of textiles

Following the procedure of Example 43(b), the suspension according to (a) is applied by direct spread coating in a quantity of 100 g/m² to either side of a non-pretreated polyamide fabric weighing 180 g/m² and reacted to completion in a drying tunnel at 130° C. to form the polyurethane (urea). The elastomeric coating shows excellent adhesion to the polyamide fabric.

Flexural strength (as measured with Bally Flexometer) is good both at room temperature and also at −10 C. (10,000 and 20,000 flexes, respectively).

What is claimed is:

1. A process for the production of solid polyisocyanates stabilized by a polymer coating and showing retarded reactivity comprising reacting
   (1) one or more solid polyisocyanates in particulate form, said polyisocyanates having melting points above 30° C., and
   (2) from 0.1 to 25 equivalent percent of amine per isocyanate equivalent of a compound having a molecular weight of from 32 to 6000, said compound being selected from the group consisting of
      (a) organic compounds containing one or more terminal —CO—NH—NH₂ groups,
      (b) hydrazines, and
      (c) mixtures thereof,
   said reaction being conducted at a temperature below the melting temperature of said solid polyisocyanate and being conducted in the presence of
   (3) a liquid medium selected from the group consisting of
      (a) organic compounds containing one or more hydroxy groups and having molecular weights of from 62 to 6000,
      (b) organic compounds containing 2 or more aromatically-bound amino groups and having molecular weights of from 108 to 6000, (c) organic compounds containing 2 or more aliphatically-bound amino groups and having molecular weights of from 400 to 6000,
(d) plasticizers,
(e) water, and
(f) mixtures thereof to form a suspension of polyadduct-coated, stabilized polyisocyanate in the liquid medium.

2. The process of claim 1 wherein the particle size of the solid polyisocyanate is from 0.5 to 200 μm.

3. The process of claim 2 wherein the particle size of said solid polyisocyanate is from 1 to 50 μm.

4. The process of claim 1 wherein the reaction is conducted additionally in the presence of an apolar or slightly polar solvent.

5. The process of claim 4 further including the step of isolating the stabilized polyisocyanate from the liquid medium.

6. The process of claim 1 further comprising the steps of suspending the stabilized polyisocyanate in a compound selected from the group consisting of (i) organic compounds containing 2 or more hydroxyl groups and having molecular weights of from 400 to 600, (ii) organic compounds containing 2 or more aromatically and/or aliphatically-bound amino groups and having molecular weights of from 400 to 6000, and (iii) mixtures thereof.

7. The process of claim 1 wherein said compound (2) is selected from the group consisting of hydrazine, alkyl hydrazines, N,N'-dialkyl hydrazines and mixtures thereof, wherein the alkyl substituent contains from 1 to 6 carbon atoms.

8. The process of claim 1 wherein said compound (2) is a hydrazine having a molecular weight of from 32 to 198.

9. The process of claim 1 wherein said compound (2) is a compound containing 1 or more terminal —CO—NH—NH$_2$ groups.

10. The process of claim 9 wherein said compound (2) has a molecular weight of from 90 to 3000.

11. The process of claim 1 wherein said liquid medium is selected from the group consisting of (i) organic compounds containing two or more aromatically-bound amino groups and having molecular weights of from 400 to 6000, (ii) organic compounds containing two or more aliphatically-bound amino groups and having molecular weights of from 400 to 6000, and (iii) mixtures thereof.

12. The process of claim 1 wherein said solid polyisocyanate has a melting point of above 80° C.

13. The process of claim 12 wherein said solid polyisocyanate is selected from the group consisting of 1,5-naphthalene diisocyanate, 1,4-phenylene diisocyanate, 3,3'-diisocyanato-4,4'-dimethyl-N,N'-diphenyl urea, dimeric 1-methyl-2,4-diisocyanatobenzene, dimeric 4,4'-diisocyanatodiphenyl methane, and 3,3'-dimethyl-4,4'-diisocyanato diphenyl.

14. The process of claim 1 characterized in that said compound (2) is used in a quantity of from 0.1 to 8 equivalent percent of amine per isocyanate equivalent.

15. The process of claim 14 wherein said compound (2) is used in a quantity of from 0.3 to 3 equivalent percent of amine per isocyanate equivalent.

16. The process of claim 1 wherein said reaction is conducted in the presence of a liquid medium selected from the group consisting of (i) organic compounds containing two or more hydroxyl groups and having molecular weights of from 400 to 6000, (ii) organic compounds containing two or more aromatically-bound amino groups and having molecular weights of from 400 to 6000, (iii) organic compounds containing two or more aliphatically-bound amino groups and having molecular weights of from 400 to 6000, and (iv) mixtures thereof.

17. The process of claim 16 wherein said liquid medium additionally contains organic compounds containing two or more hydroxy groups and having molecular weights of from 62 to 399 and/or aromatic polyamines having molecular weights of from 108 to 399.

18. The process of claim 1 characterized in that the components are reacted in quantities corresponding to a formulation for the production of a one-component polyurethane system.

19. Polyadduct-coated, stabilized, solid, finely particulate isocyanates having retarded reactivity produced by the process of claim 1 characterized by a residual isocyanate content of from at least 75% to less than 99.9% of the isocyanate groups originally present in the unstabilized solid polyisocyanate, and further characterized by a thickening temperature of the suspension of greater than 55° C.

20. The polyisocyanate of claim 19 wherein the residual NCO-content is from 92 to 99.7%.

21. The polyisocyanate of claim 20 wherein the residual isocyanate content is from 97 to 99.7%.

22. The polyisocyanate of claim 19 characterized as having a solids content of polyadduct-coated polyisocyanates of from 3 to 70% by weight in the suspension.

23. Polyadduct-coated, stabilized, solid, finely particulate polyisocyanates having retarded reactivity produced by the process of claim 7 and characterized by a residual isocyanate content of from at least 75% to less than 99.9% of the isocyanate groups originally present in the unstabilized polyisocyanates and by a thickening temperature of the suspension above 55° C.

24. Polyadduct-coated, stabilized, solid, finely particulate polyisocyanates having retarded reactivity produced by the process of claim 9 and characterized by a residual isocyanate content of at least 75% and less than 99.9% of the isocyanate groups originally present in the unstabilized polyisocyanates and further characterized by a thickening temperature of the suspension above 55° C.

25. Polyadduct-coated, stabilized, solid, finely particulate polyisocyanates having retarded reactivity produced by the processes of any one of claim 11, claim 16, or claim 17, and characterized by a residual isocyanate content of from at least 75% to less than 99.9% of the isocyanate groups originally present in the unstabilized polyisocyanates and by a thickening temperature of the suspension of above 55° C.

26. In the process of producing polyurethanes from
(A) polyisocyanates,
(B) relatively high molecular weight polyhydroxyl and/or polyamino compounds,
(C) optionally, low molecular weight chain-extending agents,
(D) optionally, catalysts and,
(E) optionally, other auxiliaries and additives,
the improvement wherein said components A and B are supplied in the form of a suspension produced in accordance with claim 1.

27. In the process of producing polyurethanes from
(A) polyisocyanates,
(B) relatively high molecular weight polyhydroxyl and/or polyamino compounds, (C) optionally, low molecular weight chain-extending agents,
(D) optionally, catalysts and,
(E) optionally, other auxiliaries and additives,
the improvement wherein said components A and B are supplied in the form of a suspension produced in accordance with claim 7.

28. In the process of producing polyurethanes from
(A) polyisocyanates,
(B) relatively high molecular weight polyhydroxyl and/or polyamino compounds,
(C) optionally, low molecular weight chain-extending agents,
(D) optionally, catalysts and,
(E) optionally, other auxiliaries and additives,
the improvement wherein said components A and B are supplied in the form of a suspension produced in accordance with claim 9.

29. In the process of producing polyurethanes from
(A) polyisocyanates,
(B) relatively high molecular weight polyhydroxyl and/or polyamino compounds,
(C) optionally, low molecular weight chain-extending agents,
(D) optionally, catalysts and,
(E) optionally, other auxiliaries and additives,
the improvement wherein said components A and B are supplied in the form of a suspension produced in accordance with claim 11, 16, or 17.

30. The process of claim 26 wherein the isocyanate/-(amine+hydroxyl)-equivalent ratio of A/(B+C) in the polyurethane forming reaction is in the range of from 0.5:1 to 1.5:1.

31. A process for the production of solid polyisocyanates stabilized by a polymer coating and showing retarded reactivity comprising reacting
(1) one or more solid polyisocyanates in particulate form, said polyisocyanates having melting points above 30° C., and
(2) from 0.1 to 25 equivalent percent of amine per isocyanate equivalent of a compound having a molecular weight of from 32 to 6000, said compound being selected from the group consisting of
 (a) organic di- or higher functional compounds containing 2 or more aliphatically-bound primary and/or secondary amino groups,
 (b) organic compounds containing one or more terminal —CO—NH—NH₂ groups,
 (c) hydrazines, and
 (d) mixtures thereof
said reaction being conducted at a temperature below the melting temperature of said solid polyisocyanate, and being conducted in the presence of
(3) a liquid medium selected from the group consisting of
 (a) organic compounds containing 2 or more aromatically-bound amino groups and having molecular weights of from 108 to 6000,
 (b) organic compounds containing 2 or more aliphatically-bound amino groups and having molecular weights of from 400 to 6000,
 (c) plasticizers,
 (d) water, and
 (e) mixtures thereof to form a suspension of polyadduct-coated, stabilized polyisocyanate in the liquid medium.

32. The process of claim 31 wherein the particle size of the solid polyisocyanate is from 0.5 to 200 μm.

33. The process of claim 32 wherein the particle size of said solid polyisocyanate is from 1 to 50 μm.

34. The process of claim 31 wherein the reaction is conducted additionally in the presence of an apolar or slightly polar solvent.

35. The process of claim 34 further including the step of isolating the stabilized polyisocyanate from the liquid medium.

36. The process of claim 31 further comprising the steps of suspending the stabilized polyisocyanate in a compound selected from the group consisting of (i) organic compounds containing 2 or more hydroxyl groups and having molecular weights of from 400 to 6000, (ii) organic compounds containing 2 or more aromatically and/or aliphatically-bound amino groups and having molecular weights of from 400 to 6000, and (iii) mixtures thereof.

37. The process of claim 31 wherein said compound (2) is an organic di- or higher functional compound containing two or more aliphatically-bound primary and/or secondary amino groups having a molecular weight from 60 to 3000.

38. The process of claim 31 wherein said compound (2) is a compound of the group (2)(a), wherein said liquid medium is selected from the group of (3)(b), and wherein said compound (2) and said liquid medium (3) are the same compound.

39. The process of claim 31 wherein said liquid medium is selected from the group consisting of (i) organic compounds containing two or more aromatically-bound amino groups and having molecular weights of from 400 to 6000, (ii) organic compounds containing two or more aliphatically-bound amino groups and having molecular weights of from 400 to 6000, and (iii) mixtures thereof.

40. The process of claim 31 wherein said solid polyisocyanate has a melting point of above 80° C.

41. The process of claim 40 wherein said solid polyisocyanate is selected from the group consisting of 1,5-naphthalene diisocyanate, 1,4-phenylene diisocyanate, 3,3'-diisocyanato-4,4'-dimethyl-N,N'-diphenyl urea, dimeric 1-methyl-2,4-diisocyanatobenzene, dimeric 4,4'-diisocyanato-diphenylmethane and 3,3'-dimethyl-4,4'-diisocyanato-diphenyl.

42. The process of claim 31 characterized in that said compound (2) is used in a quantity of from 0.1 to 8 equivalent percent of amine per isocyanate equivalent.

43. The process of claim 42 wherein said compound (2) is used in a quantity of from 0.3 to 3 equivalent percent of amine per isocyanate equivalent.

44. The process of claim 31 wherein said reaction is conducted in the presence of a liquid medium selected from the group consisting of (i) organic compounds containing two or more aromatically-bound amino groups and having molecular weights of from 400 to 6000, (ii) organic compounds containing two or more aliphatically-bound amino groups and having molecular weights of from 400 to 6000, and (iii) mixtures thereof.

45. The process of claim 44 wherein said liquid medium additionally contains organic compounds containing two or more hydroxy groups and having molecular weights of from 62 to 399 and/or aromatic polyamines having molecular weights of from 108 to 399.

46. The process of claim 31 characterized in that the components are reacted in quantities corresponding to a formulation for the production of a one-component polyurethane system.

47. Polyadduct-coated, stabilized, solid, finely particulate isocyanates having retarded reactivity produced by the process of claim 31, characterized by a residual isocyanate content of from at least 75% to less than 99.9% of the isocyanate groups originally present in the unstabilized solid polyisocyanate, and further characterized by a thickening temperature of the suspension of greater than 55° C.

48. In the process of producing polyurethanes from
(A) polyisocyanates,
(B) relatively high molecular weight polyhydroxyl and/or polyamino compounds,
(C) optionally, low molecular weight chain-extending agents,
(D) optionally, catalysts and,
(E) optionally, other auxiliaries and additives,
the improvement wherein said components A and B are supplied in the form of a suspension produced in accordance with claim 31.

49. The process of claim 48 wherein the isocyanate/-(amine+hydroxyl)-equivalent ratio of A/(B+C) in the polyurethane forming reaction is in the range of from 0.5:1 to 1.5:1.

50. A process for the production of solid polyisocyanates stabilized by a polymer coating and showing retarded reactivity comprising
(A) reacting:
(1) one or more solid polyisocyanates in particulate form, said polyisocyanates having melting points above 30° C., and
(2) from 0.1 to 25 equivalent percent of amine per isocyanate equivalent of a compound having a molecular weight of from 32 to 6000, said compound being selected from the group consisting of
(a) organic di- or higher functional compounds containing 2 or more aliphatically-bound primary and/or secondary amino groups,
(b) organic compounds containing one or more terminal —CO—NH—NH$_2$ groups,
(c) hydrazines, and
(d) mixtures thereof,
said reaction being conducted at a temperature below the melting temperature of said solid polyisocyanate, and being conducted in the presence of an organic compound containing one or more hydroxyl groups and having molecular weights of from 400 to 6000 to form a suspension of polyadduct-coated, stabilized polyisocyanate,
(B) adding to the suspension one or more organic compounds containing 2 or more aromatically-bound amino groups and having molecular weights of from 108 to 399.

51. The product of claim 50.

52. In the process of producing polyurethanes from
(A) polyisocyanates,
(B) relatively high molecular weight polyhydroxyl and/or polyamino compounds,
(C) optionally, low molecular weight chain-extending agents,
(D) optionally, catalysts and,
(E) optionally, other auxiliaries and additives, the improvement wherein said components A, B and C are supplied in the form of a suspension produced in accordance with claim 50.

* * * * *